(12) United States Patent
Nakazawa et al.

(10) Patent No.: US 6,699,195 B2
(45) Date of Patent: Mar. 2, 2004

(54) ELECTRONIC BLOOD PRESSURE MONITOR AND BLOOD PRESSURE DATA PROCESSING SYSTEM

(75) Inventors: Fumio Nakazawa, Kyoto (JP); Kiyoshi Sakai, Kyoto (JP); Koichi Takizawa, Kyoto (JP)

(73) Assignee: Omron Corporation, Kyoto (JP)

( * ) Notice: Subject to any disclaimer, the term of this patent is extended or adjusted under 35 U.S.C. 154(b) by 0 days.

(21) Appl. No.: 10/228,254

(22) Filed: Aug. 27, 2002

(65) Prior Publication Data
US 2003/0060721 A1 Mar. 27, 2003

(30) Foreign Application Priority Data
Aug. 27, 2001 (JP) ........................................ 2001-256156

(51) Int. Cl.[7] ................................................. A61B 5/02
(52) U.S. Cl. ....................................... 600/485; 600/300
(58) Field of Search ................................. 600/300–301, 600/485, 490–496

(56) References Cited
U.S. PATENT DOCUMENTS 5,833,619 A * 11/1998 Freed et al. ................ 600/485
5,967,975 A * 10/1999 Ridgeway ................... 600/300
6,149,586 A * 11/2000 Elkind ......................... 600/300
6,450,955 B1 * 9/2002 Brown et al. ............... 600/300
6,511,435 B1 * 1/2003 Bluth et al. ................. 600/490
6,524,239 B1 * 2/2003 Reed et al. .................. 600/300
6,612,984 B1 * 9/2003 Kerr, II ....................... 600/300

* cited by examiner

Primary Examiner—Max F. Hindenburg
Assistant Examiner—Patricia Mallari
(74) Attorney, Agent, or Firm—Morrison & Foerster LLP

(57) ABSTRACT

In a blood pressure monitor, time habit data representing daily time habits of a patient and a plurality of timings for blood pressure measurement determined by a medical doctor are inputted. The predetermined timings are variably adjusted based on the daily time habit data, and results of blood pressure measurements at the specified timings are stored in a memory. A personal computer for the doctor of a medical facility receives and outputs information read out from the memory of the blood pressure monitor. Accordingly, blood pressure measurements can be performed in timings adjusted in accordance with the daily habit pattern of the patient, so that more accurate measurement can be achieved. Because information including such measurement data is presented to the doctor with diagnostic authority via the personal computer, the doctor can acquire useful information for assisting diagnosis and treatment of hypertension symptoms of the patient.

33 Claims, 16 Drawing Sheets

Fig. 7

| D1 | D11: TERMINAL IDENTIFICATION CODE | 00009876 |
| --- | --- | --- |
| | D12: PATIENT CODE | 54321 |
| | D13: MEDICAL FACILITY CODE | 1234567 |
| | D14: DOCTOR CODE | 12345 |
| | D15: PASSWORD | ABC975H |
| | D16: PATIENT RECORD NO. CODE | AB12345 |

| D2 | MEASUREMENT INSTRUCTION DATA | 1 |
| --- | --- | --- |
| | D21 — WHITE-COAT HYPERTENSION CLASSIFICATION | 1 |
| | D22 — DIPPER CLASSIFICATION | 1 |
| | D23 — MORNING SERGE CLASSIFICATION | 1 |
| | ⋮ | ⋮ |
| | CHALLENGE SETTING DATA | 1 |
| | D24: NO SMOKING | 0 |
| | D: 25DIETING | 0 |
| | D: 26WALKING | 1 |
| | ⋮ | ⋮ |

| D3 | | | |
| --- | --- | --- | --- |
| | YEAR/MONTH/DAY/HOUR/MINUTE | 0107010830 | D31 |
| | MAXIMUM BLOOD PRESSURE VALUE | 123.00 | |
| | MINIMUM BLOOD PRESSURE VALUE | 89.00 | |
| | HEART RATE | 67 | |
| | PLACE | HOME (OUTPATIENT) | |
| | YEAR/MONTH/DAY/HOUR/MINUTE | 0107012230 | D32 |
| | MAXIMAL BLOOD PRESSURE VALUE | 110.00 | |
| | MINIMAL BLOOD PRESSURE VALUE | 80.00 | |
| | HEART RATE | 65 | |
| | PLACE | HOME (OUTPATIENT) | |
| | ⋮ | ⋮ | D3i ... D3n |

| D4: ANALYSIS AND JUDGMENT RESULT DATA GROUP |
| --- |
| D5: SPECIAL EVENT DATA GROUP |

Fig. 10

A, B, ... EACH REPRESENTS MEASUREMENT DATA OR CALCULATED DATA, AND IN THIS CASE MAXIMUM BLOOD PRESSURE IS EMPLOYED FOR ALL DATA

| | | | |
|---|---|---|---|
| FIRST MEASUREMENT (DIRECTLY AFTER WAKEUP) | A | | |
| SECOND MEASUREMENT | B | B/A | ≧130% → (MS) |
| AVERAGE BLOOD PRESSURE VALUE OF 24 HOURS | C | D/C OR D/C' | LESS THAN 100% → (in-D) |
| DAY-TIME BLOOD PRESSURE VALUE | D | | 100% OR MORE TO LESS THAN 110% → (non-D) |
| NIGHT-TIME BLOOD PRESSURE VALUE | C' | | 110% OR MORE TO LESS THAN 120% → (D) |
| | | | 120% OR MORE → (ex-D) |
| OUTPATIENT BLOOD PRESSURE VALUE | E | E/D | 110% OR MORE → (WH) |

TIME-VARIATION MONITOR $A_m \to A_n, B_m \to B_n, (B/A)_m \to (B/A)_n$
$C_m \to C_n, D_m \to D_n, (D/C)_m \to (D/C)_n$

M: AVERAGE IN SINGLE DAY OVER CERTAIN PERIOD
N: AVERAGE IN SINGLE DAY OVER CERTAIN PERIOD AFTER LAPSE OF CERTAIN PERIOD FROM "M"

ELECTRONIC BLOOD PRESSURE MONITOR AND BLOOD PRESSURE DATA PROCESSING SYSTEM

BACKGROUND OF THE INVENTION

1. Field of the Invention

This invention relates to an electronic blood pressure monitor and a blood pressure data processing system for processing results of measurement which are obtained by electronically measuring blood pressures, and in particular, to an electronic blood pressure monitor and a blood pressure data processing system capable of assisting diagnosis and treatment of hypertension in a subject.

2. Background of the Invention

Conventionally, when a person with the authority to diagnose a patient diagnoses and treats an outpatient on the basis of blood pressure values of the patient, the blood pressure values are not necessarily considered to be reliable values since they are results of a measurement performed when the patient is at a medical facility. That is, blood pressure values are variable even within a day, as well as influenced by additional body activity due to the visit to the hospital. Also, the phenomenon of "white-coat hypertension" is known, so-called because it is induced by the patient's seeing a doctor wearing a white laboratory coat, so that diagnosing and treating hypertension based on blood pressure values taken when a patient is at a medical facility has been viewed with suspicion. Hence there has been a demand for a blood pressure measurement system which is useful for properly measuring blood pressures which are representative of blood pressures of the patient and for diagnosing and treating hypertension.

Conventionally, there have been a few examples of measuring blood pressures in a daily life outside a hospital, in which a patient herself/himself regularly measures blood pressures and records the result of the measurement every day and at predetermined times under the instruction of a person with the authority. In the manner as described above, however, the patient may forget the measurements to be performed at the predetermined times, or may be in a condition in which measurement is impossible, or the measurement data may not be recorded properly, and additionally, measurement of blood pressure cannot be performed when the patient is asleep. Accordingly, it has been impossible to properly measure blood pressure values throughout the daily life of the patient.

In view of the above, a portable blood pressure monitor is provided. A patient always wears a small blood pressure monitor, and by automatically measuring blood pressures every certain time, for example, every 15 minutes, variations in blood pressures over 24 hours can be ascertained. Also new clinical findings have been obtained based on the result of such measurements.

In such a portable blood pressure monitor, however, blood pressure values obtained in the measurements performed while the patient is moving lack reliability, and the patient always wears the blood pressure monitor including the sleeping time, so that the influence exerted on the daily life of the patient is significant, and stress caused by taking the measurement every 15 minutes cannot be ignored, making it difficult to continue the measurement for a long period of time.

As disclosed in Japanese Unexamined Patent Publication JP-A 8-275927 (1996), for example, a medical system has been proposed wherein communication means are provided between a patient at home and a medical facility, obtained blood pressure values and the like are transmitted to the medical facility, and thereby the contents of interview and instruction can be transmitted to the patient from a person with the authority to diagnose the patient. Alternatively, as disclosed in Japanese Unexamined Patent Publication JP-A 5-137697 (1993), a portable blood pressure monitor capable of inputting event times for blood pressure measurement, for example, such as after administration of medicine, after meals, just before going to bed, just after waking up, and capable of storing these events together with the measured blood pressure values has been proposed.

However, a data processing system for diagnosing and treating a patient having hypertension has not been proposed yet, and a system which is useful for both a patient having hypertension and a person with authority to diagnose the patient has not been proposed yet.

As described above, it is the current situation that not only does a blood pressure monitor suited for measurement at home for patients having hypertension and prospective patients having hypertension not exist, but also a tool capable of assisting diagnosis by sending information such as blood pressure measurement data, measurement time and the like to a person with the authority to diagnose the patient from the patient having hypertension and capable of judging the hypertension based on the obtained data does not exist. For this reason, it has been impossible to effectively control the blood pressure values which otherwise could be a matter of life or death, and increases in medical fees due to wasteful administration of medicine and unsuitable treatment have occurred.

SUMMARY OF THE INVENTION

Accordingly, this invention is directed to providing an electronic blood pressure monitor and a blood pressure data processing system capable of assisting diagnosis and treatment of hypertension symptoms or the like.

An electronic blood pressure monitor according to an aspect of this invention includes a measuring portion configured to measure a blood pressure of a subject and an output portion outputting data including results of the blood pressure measurement, and further may include a first input interface inputting time habit data, a second input interface inputting measurement pattern data and a timing adjustment device.

As time data indicating a time habit of the subject is inputted by the first input interface for inputting time habit data, and pattern data specifying a certain timing of a plurality of blood pressure measurements by the measuring portion is inputted by the second input interface for inputting pattern data, the timing adjustment device variably adjusts the timing of a plurality of measurements defined by the inputted pattern data based on the inputted time habit data of the subject.

Therefore, as a person with the authority to diagnose the subject inputs pattern data and designates a timing of a plurality of blood pressure measurements, the designated timing of the plurality of blood pressure measurements is variably adjusted in accordance with the time data indicating the daily habits of the subject, and the measurements are performed according to a schedule that has been so adjusted. Accordingly, blood pressure measurements can be performed according to a schedule which has been adjusted in accordance with the daily habits of the subject, with the result that more accurate measurements are achieved. By presenting such data including the results of measurements via the output portion, it is possible to provide information which is useful for assisting diagnosis and treatment of hypertension symptoms of the subject.

The electronic blood pressure monitor as described above further includes an alarming device for notifying a time of blood pressure measurement based on the timing altered by the timing adjustment device.

Therefore, since an alarm for notifying blood pressure measurement is issued for the subject every timing of blood pressure measurement, it is possible to prevent the subject from missing or forgetting the blood pressure measurement times.

In the above-described blood pressure monitor, the timing of the blood pressure measurements defined by the measurement pattern data is configured to diagnose hypertension of the subject.

Therefore, the predetermined timings for diagnosing hypertension of the subject can be variably adjusted in accordance with the daily habits of the subject, so that more correct diagnosis is realized.

The above-described blood pressure monitor further includes a first input portion providing the first input interface and a second input portion providing the second input interface, the second input portion being accessible only to a person with the authority to diagnose the subject.

Therefore, since a third party including the subject other than a person with the authority to diagnose the subject is not allowed to operate the second input portion, it is possible to securely prevent the pattern data defining the predetermined timings of blood pressure measurement inputted by external operation of the second input portion by a person with the authority to diagnose the subject from being changed by such a third party.

The above-described electronic blood pressure monitor further includes an event input interface inputting an event occurrence data into the blood pressure monitor, and the event input interface includes a first event input portion disposed on the first input portion.

Therefore, the subject can input events which occur in his or her daily life and have influence on the blood pressure measurement (for example, exercise, driving cars, meals, smoking, drinking and the like) at any time by operating the first input portion.

The above-described electronic blood pressure monitor further includes an event input interface for inputting event occurrence data into the blood pressure monitor, and the event input interface includes a second event input portion disposed on the second input portion.

Therefore, a person with the authority to diagnose the subject can input events occurring in the daily life of the subject that are determined the influential on the blood pressure measurement by operating the second event input portion.

The event occurrence data inputted by the second event input interface may be used by the blood pressure monitor to display therapeutic instructions, such as exercise, dieting or no smoking, from a person with authority to diagnose the subject, and may provide a record of administering medicine to the subject.

The computation of the above-described blood pressure monitor includes calculating a difference between the results of the measurements before and after a passage of a predetermined time from the start of administering the medicine.

Therefore, in the case of administering medicine such as an antihypertensive, it is possible to display assisting data for diagnosing the effect of the administration.

The above-described blood pressure monitor further includes a memory portion storing data including the time habit data, the measurement pattern data and the measurement data, the measurement data being stored in the memory portion chronologically.

Therefore, since a chronological change in measurement data can be confirmed by reading out the measurement data stored in the memory portion, it is possible to provide a more appropriate diagnosis.

The above-described blood pressure monitor further includes an event input interface inputting event occurrence data into the blood pressure monitor, the event occurrence data being stored in the memory portion chronologically, and an event corresponding to the event occurrence data has an influence on the blood pressure measurements.

Therefore, since a chronological change in measurement data and chronological occurrences of events in association with daily life that will influence on the blood pressure measurement are represented by reading out the measurement data stored in the memory portion, it is possible to determine a correlation between the change in measurement data and the occurrences of the events that will influence on the blood pressure measurement.

The above-described blood pressure monitor further includes a computation portion which selects a set of the measurement data stored in the memory portion based on selection criteria for hypertension diagnosis, performs a computation on the selected data based on computation criteria for hypertension diagnosis, performs a judgment on a result of the computation based on judging criteria for hypertension diagnosis, and transfers a result of the judgment to the output portion.

Therefore, in this blood pressure monitor, since a set of the measurement data is selected based on selection criteria for hypertension diagnosis, and the set of the measurement data is subjected to computation and the computation result is judged, and the judgment result is outputted, so that it is possible to provide an index for assisting the diagnosis of hypertension.

In the above-described blood pressure monitor, a readout from the memory portion is allowed only for a person with the authority to diagnose the subject. Therefore, it is possible to prevent the measurement data or the judgment data or the event data stored in the memory portion from being read out by a third party other than a person with the authority to diagnose the subject, which reduces the likelihood of invasion of privacy of the subject and the illegal falsification of stored data.

The memory portion may be detachably mounted on the blood pressure monitor. This provides convenience for the subject since the subject can bring just the memory portion to the medical facility and have a diagnosis.

In the above-described blood pressure monitor, the result of the judgment is stored in the memory portion. Therefore, by temporarily storing the above-described index for assisting the hypertension diagnosis in the memory portion and reading out the same index at a medical facility or the like, it is possible to provide information for assisting diagnosis and prescription of medication.

In the computation in the above-described electronic blood pressure monitor, the plurality of the blood pressure measurements includes a first measurement performed when the subject wakes up, a second measurement performed when the subject completes a day's work, and a third measurement performed when the subject goes to bed, and the computation includes dividing a result of the second measurement by a result of the third measurement or an average of a result of the first measurement and the result of the third measurement.

In the computation in the above-described electronic blood pressure monitor, the plurality of the blood pressure measurements includes night-time measurements performed when the subject is asleep and day-time measurements performed when the subject is awake, and the computation includes calculating an average of results of the night-time measurements, calculating an average of results of the day-time measurements, a first day-time measurement and a last day-time measurement being excluded from the average computation, and dividing the average of the results of the day-time measurements by the average of the results of the night-time measurements.

In the computation in the above-described electronic blood pressure monitor, the plurality of the blood pressure measurements includes day-time measurements performed when the subject is awake, and the computation includes calculating an average of results of the day-time measurements, a first day-time measurement and a last day-time measurement being excluded from the average computation, calculating an average of results of the first and last day-time measurements, and dividing the average of the results of the day-time measurements by the result of the last day-time measurement or the average of the results of the first and last day-time measurements.

In the computation in the above-described electronic blood pressure monitor, the plurality of the blood pressure measurements includes night-time measurements performed when the subject is asleep and a day-time measurement performed when the subject completes a work of a day, and the computation includes calculating an average of results of the night-time measurements, and dividing the day-time measurement by the average of the results of the night-time measurements.

By the computation process as described above, an index for diagnosing the inverted dipper (night-time blood pressure is higher than day-time blood pressure or 24-hour average blood pressure), non-dipper (an increase in day-time blood pressure is slight with respect to night-time blood pressure), dipper (a decrease in night-time blood pressure is normal) or extreme dipper (the decrease is excessive) can be outputted as a result of the process.

In the computation in the above-described electronic blood pressure monitor, the plurality of the blood pressure measurements includes a first measurement performed when the subject wakes up and a second measurement performed when a predetermined time passes after the first measurement, and the computation includes dividing a result of the second measurement by a result of the first measurement.

By this computation process, it is possible to output an index for diagnosing the morning surge (rapid blood pressure rising in the early morning) as a result of the process.

In the computation in the above-described electronic blood pressure monitor, the plurality of the blood pressure measurement includes day-time measurement performed when the subject is awake, and the computation includes calculating an average of results of the day-time measurements, a first day-time measurement and a last day-time measurement being excluded from the average calculation, calculating an average of results of the first and last day-time measurements, and dividing a result of a blood pressure measurement performed on the subject when the subject is at a medical facility with the authority to diagnose the subject by the average of the results of the day-time measurements, the result of the blood pressure measurement performed at the medical facility being stored in the memory portion.

The blood pressure measurement at the medical facility is performed when a person with the authority to diagnose the subject is with the subject.

By such a computation process, it is possible to output an index for diagnosing the presence/absence of white-coat hypertension (becoming tense in front of a person with the authority (wearing a white coat, for example) to diagnose the subject to cause increase in blood pressure) as a result of the process.

The above-described electronic blood pressure monitor further includes an event input interface inputting an event occurrence data into the blood pressure monitor, the event occurrence data being stored in the memory portion chronologically, and the computation includes calculating a difference of the result of the measurements before and after an occurrence of an event specified by the event occurrence data. In this computation process, the result of the measurement after an occurrence of an event specified by the event occurrence data read out from the memory portion may be divided by the result of the measurement before the occurrence of the event specified by the event occurrence data read out from the memory portion. Alternatively, averages of the result of the measurements before and after an occurrence of an event specified by the event occurrence data read out from the memory portion may be calculated, and the average of the measurement after an occurrence of an event may be divided by the average of the measurement before an occurrence of the event.

Therefore, it is possible to ascertain the relationship between the result of the blood pressure measurement and events that influence the blood pressure measurement in association with daily life.

A blood pressure data processing system according to another aspect of this invention includes an electronic blood pressure monitor configured to measure the blood pressure of a subject and to output measurement data including a result of a blood pressure measurement and an information processing system receiving the measurement from the electronic blood pressure monitor.

The electronic blood pressure monitor includes a timing adjustment portion which receives time habit data indicative of a daily habit pattern of the subject and measurement pattern data identifying a timing of a plurality of blood pressure measurements on the subject, and alters the timing of the measurements defined by the measurement pattern data based on the time habit data of the subject, and a memory portion storing data including the measurement data.

The information processing system includes an information reception device receiving the measurement data read out from the memory portion of the electronic blood pressure monitor in response to a read request and an output device outputting the measurement data received by the information receiving device.

Therefore, at the electronic blood pressure monitor, if a person with the authority to diagnose the subject or the like designates and inputs a plurality of predetermined timings of blood pressure measurement, the designated plurality of predetermined timings are variably adjusted on the basis of the time habit data indicative of a daily habit pattern of the subject, and the blood pressure measurements are performed according to the adjusted timings, while the data including the measurement data is stored in the memory portion. Then at the information processing system of the medical facility, the data stored in the memory portion is received and outputted. Accordingly, since it is possible to perform the blood pressure measurements according to timings adjusted in accordance with the daily habit pattern of the subject, more accurate measurements are enabled. Such information including measurement data is displayed via the output device of the information processing system of a medical facility, useful information for assisting the diagnosis and treatment of the hypertension symptoms of the subject can be acquired at a medical facility.

The electronic blood pressure monitor of the above-described blood pressure data processing system further includes a computing portion performing a predetermined computation on the measurement data stored in the memory portion based on criteria of hypertension diagnosis and storing the result of the computation in the memory portion.

Therefore, at a medical facility, since the result of the predetermined process for assisting the diagnosis of hypertension of the subject based on the measurement data of blood pressure of the subject is displayed via the output device of the information processing system, it is possible to acquire information useful for assisting the diagnosis and treatment of the patient's hypertension symptoms.

In the above-described blood pressure data processing system, the electronic blood pressure monitor further includes an information sending portion sending the measurement data in response to the read request, and the information processing system comprises an information receiving portion receiving the measurement data sent from the information sending portion.

Therefore, the measurement data of blood pressure stored in the memory portion of the electronic blood pressure monitor or the result of the predetermined process for assisting the diagnosis of hypertension based on the measurement data of blood pressure can be given to the information processing system of the medical facility by communication.

In the above-described blood pressure data processing system, the electronic blood pressure monitor may be configured to be directly connected to the information processing system by a data transmitting cable.

Furthermore, the communication may be established by connection via radio, public line network (including the Internet), dedicated line network or the like.

In the above-described blood pressure data processing system, the memory portion may include a detachable storage medium, the electronic blood pressure monitor may include a first medium access portion detachably engaging with the detachable storage medium and accessing the detachable storage medium engaged with the first medium access portion, and the information reception device may include a second medium access portion detachable engaging with the detachable storage medium and accessing the detachable storage medium engaged with the second medium access portion when the read request is inputted.

Therefore, the memory portion which stores the measurement data of blood pressure or the result of the predetermined process for assisting a diagnosis of hypertension based on the measurement data of blood pressure is advantageously a portable storage medium. Accordingly, after completing the blood pressure measurements, the subject removes the storage medium from the first medium access portion of the electronic blood pressure monitor and brings the same storage medium to the medical facility. At the medical facility, the storage medium provided by the subject is accessed via the second medium access portion of the information processing system, and the contents of the storage medium are read out to be displayed to a person with the authority to diagnose the subject.

In this manner, all the subject has to do is to go to the medical facility while carrying the storage medium for presenting the information for assisting a diagnosis of hypertension to a person with the authority to diagnose the subject and have a diagnosis (or prescription), which is convenient.

In the above-described blood pressure data processing system, the measurement data is read out only when the read request is verified.

Therefore, the measurement data of blood pressure from the memory portion or the result of the predetermined process for assisting a diagnosis of hypertension based on the measurement data of blood pressure may be accessed and read out only when the read request is verified. Therefore, it is possible to prevent the measurement data or the judgment data or the event data stored in the memory portion from being read out by a third party other than a person with the authority to diagnose the subject, which reduces the likelihood of invasion of privacy of the subject and the illegal falsification of stored data.

The above-described blood pressure data processing system further may include a patient record registry device for registering a patient record and a patient record management device for managing the patient record. The electronic blood pressure monitor further may include an information sending portion sending the measurement data read out from the memory portion. The patient record management device receives the measurement data sent from the information sending portion and stores the measurement data in the patient record registry device as a part of the patient record, and the information processing system receives a patient record of the subject stored in the patient record registry through the patient record management device and performs a predetermined computation on the measurement data based on criteria on hypertension diagnosis and patient record of the subject.

Therefore, information including the measurement data of blood pressure of the subject stored in the memory portion of the electronic blood pressure monitor is sent to be received by the patient record management device of the medical facility. The patient record management device registers the received information as patient record data in the patient record registry for each subject, and the information processing system reads out the patient record of the subject registered in the patient record registry and performs a predetermined process for assisting a diagnosis to output a result of the process.

Therefore, the subject may have a diagnosis (prescription) even at home by being subjected to the predetermined process by the medical facility for assisting a diagnosis based on the information including the measurement data of blood pressure of the subject.

In the above-described blood pressure data processing system, the blood pressure monitor is allowed to send the measurement data to the patient record management device only when the patient record management device verifies the blood pressure monitor.

Therefore, since the electronic blood pressure monitor is allowed to send the information including the measurement data of blood pressure of the subject to the data management device from the electronic blood pressure monitor by means of the information sending potion only when the blood pressure monitor is verified, it is possible to prevent the patient record data in the patient record registry from being interfered with by information sent from an illegal apparatus.

In the above-described blood pressure data processing system, the blood pressure monitor is connected to the patient record management device via a communication network and a network connection device.

In the above-described blood pressure data processing system, the network connection device may be a mobile communication terminal.

BRIEF EXPLANATION OF THE DRAWINGS

FIG. 7 shows an example of the contents of a blood pressure measurement data file according to certain embodiments of the invention.

FIG. 10 shows an example of an analysis and judgment procedure for diagnosis of hypertension used in this invention.

DETAILED DESCRIPTION OF THE INVENTION

In the following, embodiments of this invention will be explained with reference to the drawings.

In each embodiment, description is made for a blood pressure monitor and a blood pressure data processing system which can measure a patient's blood pressure when the patient is at home or at a hospital (outpatient), compare and verify the blood pressure, and thereby assist a hypertension diagnosis to be made by a person with the authority to diagnose the patient.

In medical diagnosis and treatment of hypertension and the like, for constructing an approach to "what kind of diagnosis to be made based on what kind of examination, and what kind of treatment (prescription) should be given", a person with the authority to diagnose a patient indicates measuring time and the like to the patient, makes an appropriate judgment on a result of measurement, prescribes an objective treatment (prescription), and provides instructions for administration of antihypertensive accurately and safely by using a blood pressure monitor and a blood pressure data processing system of this invention. In other words, a blood pressure monitor for home use is turned into a tool not only for health control as conventionally used, but also for treatment of hypertension and the like.

Figure 1A:
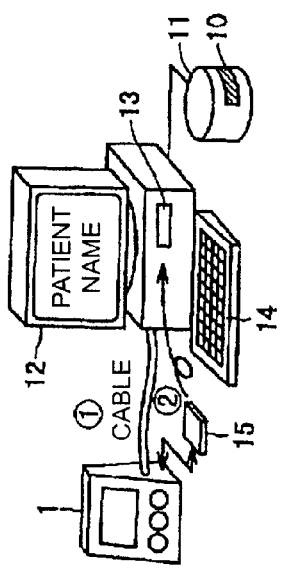
FIGS. 1A and 1B are schematic configuration views showing a blood pressure data processing system according to embodiments of this invention.
Figure 1B:
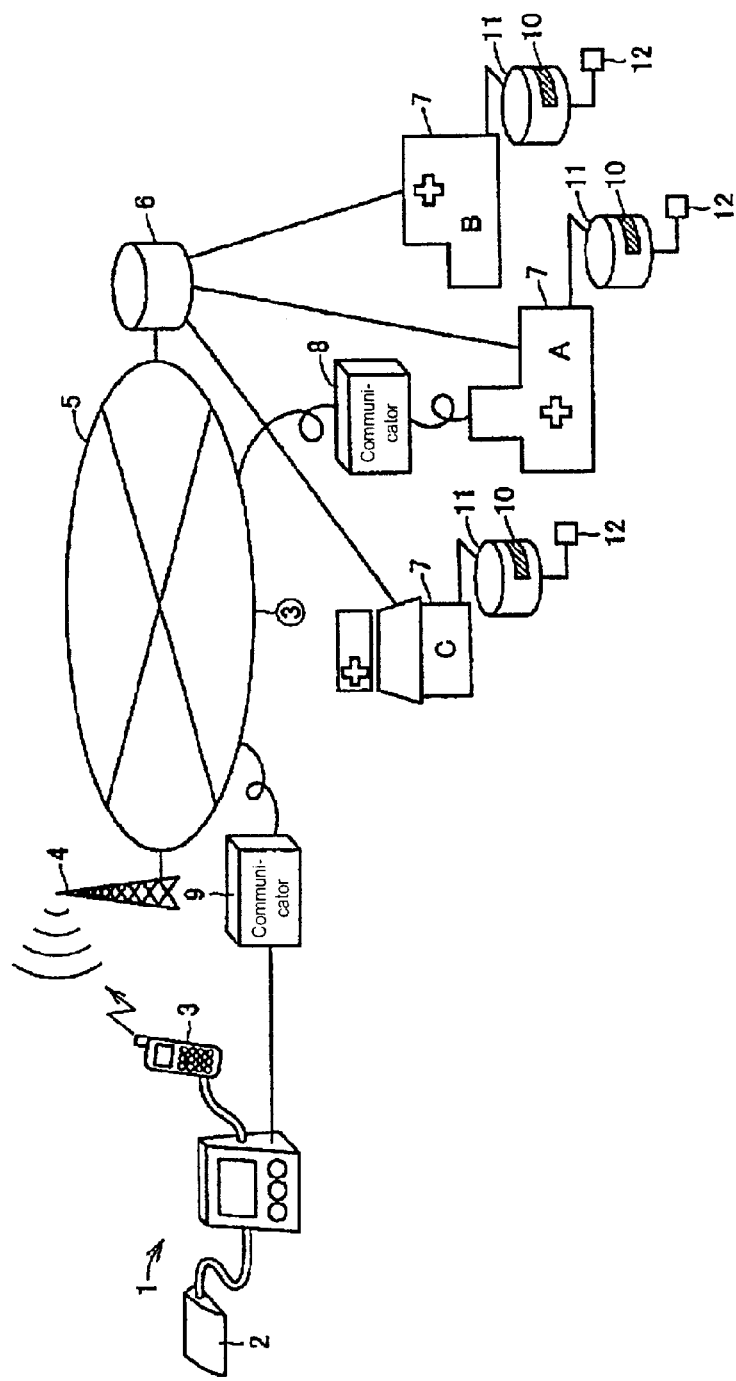

FIGS. 1A and 1B are schematic configuration views of a blood pressure data processing system according to three embodiments of this invention. When a patient who is a subject of a treatment or diagnosis measures a blood pressure using a blood pressure monitor 1 which measures blood pressure by means of an arm band or cuff 2, various information including the measurement data is stored in a memory of the blood pressure monitor 1, and then registered in a patient record data file 10 corresponding to the patient in a server apparatus 11 of a medical facility 7 such as a clinic or hospital to be used as information for treatment and diagnosis. There are three main methods for transferring data for registering various information including the measurement data in the memory of the blood pressure monitor 1 into the corresponding patient record data file 10 in the server apparatus 11: transferring methods (1) and (2) shown in FIG. 1A and transferring method (3) shown in FIG. 1B. The patient record file 10 is registered for each patient, and the server apparatus 11 manages the patient record data file 10.

The transferring method (1) shown in FIG. 1A is a method wherein a patient brings the blood pressure monitor 1 to the medical facility 7, and by direct connection via a cable with a personal computer 12, dedicated to persons with authority to diagnose the subject, the data is transferred to the corresponding patient record data file 10 in the server apparatus 11 via the cable and the personal computer 12.

Transferring method (2) is a method wherein a portable memory card 15 that has been previously mounted on the blood pressure monitor 1 is drawn out and mounted on a memory card reader/writer 13 of the personal computer 12, and the memory card reader/writer 13 makes access to the mounted memory card 15 to read out various information such as blood pressure measurement data written into the memory card 15 and transfers the data to the patient record data file 10 in the server apparatus 11. Both transferring methods (1) and (2) are off-line data transferring methods, and the on-line data transferring method (3) is shown in FIG. 1B.

In transferring method (3), various information such as blood pressure measurement data stored in the internal memory of the blood pressure monitor 1 is transferred via a mobile terminal (hereinafter, referred to as a mobile) 3 such as portable telephone set being connected with the blood pressure monitor 1, a radio base station 4 located at the closest point and a network 5 such as the Internet or a telephone network, to be stored in the corresponding patient record data file 10 in the server apparatus 11 of the medical institute 7 via a data processing center 6 or a communicator 8 corresponding to the medical facility 7. The mobile 3, the closest radio base station 4, the data processing center 6 and the communicator 8 can be regarded as relay apparatuses for communication. The network 5 is an Internet VPN (virtual private network) and the like having security. It goes without saying that in this case, the information concerning the patient is protected by encryption or provision of a password for the person with the authority to diagnose the patient to fetch the information.

The data processing center 6 is provided for a plurality of medical facilities 7, and has the function of performing collection of communication data sent to the respective medical facilities 7 and distribution of data to patient records. Alternative to the mobile 3, a communicator 9 such as personal computer may be connected to the blood pressure monitor 1 via a cable and the information stored in the internal memory of the blood pressure monitor 1 may be stored in the corresponding patient record data file 10 in the server apparatus 11 of the medical facility 7 via the communicator 9 and the network 5 in the same manner as described above.

In addition, the personal computer 12 can access the patient record data file 10 via the server apparatus 11 of the corresponding medical facility 7 via an intrahospital LAN (local area network).

First Embodiment

In the first embodiment, explanation will be mode for the case where the blood pressure monitor 1 is brought to the medical facility 7 by way of transferring method (1) as described above, and the brought-in blood pressure monitor 1 is directly connected with the personal computer 12 via a cable, whereby the data is transferred.

Figure 2:
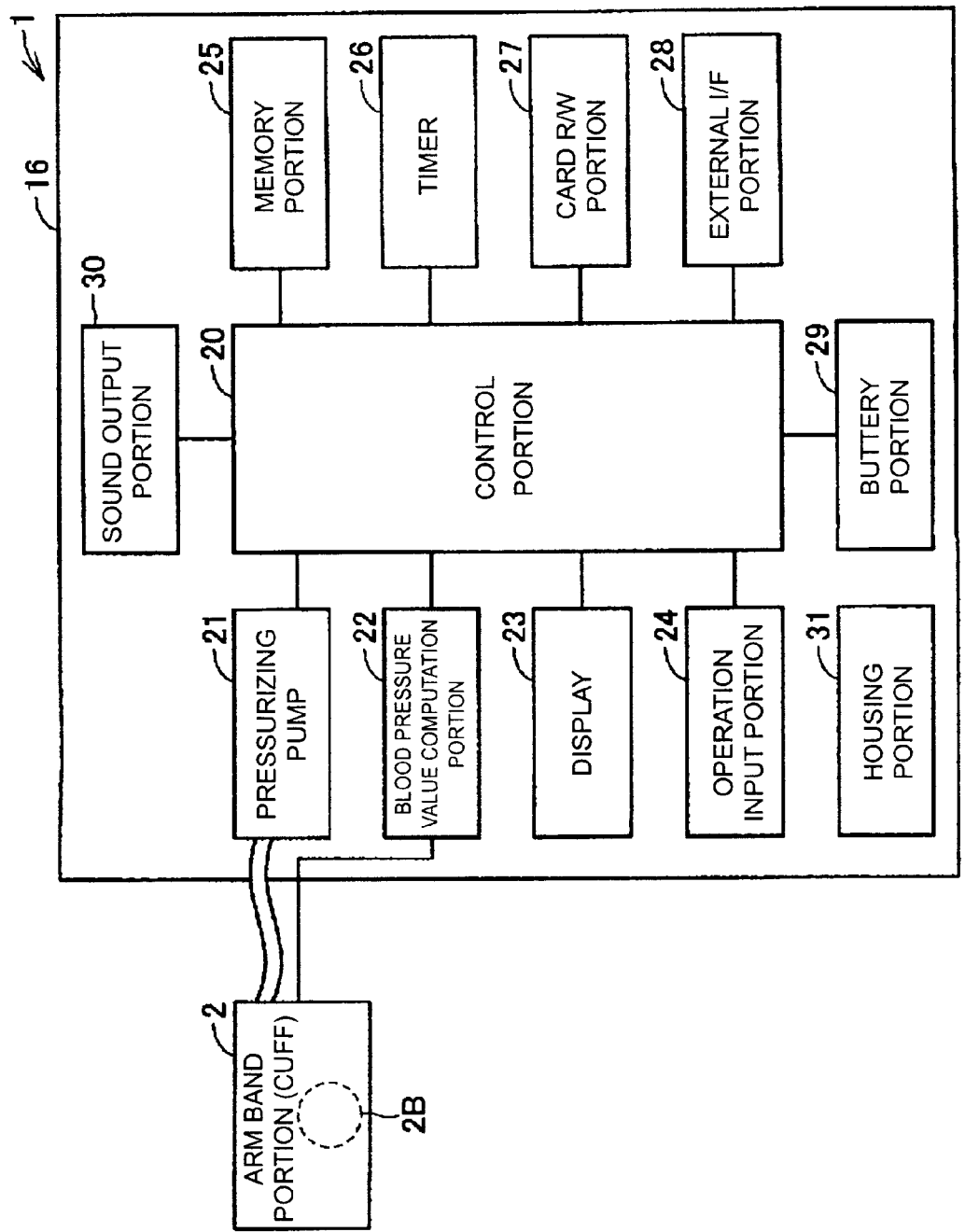
FIG. 2 is a hardware configuration of a blood pressure monitor according to these embodiments.

FIG. 2 shows a hardware configuration view of the blood pressure monitor 1 used in the first embodiment as well as the other embodiments. The blood pressure monitor 1 includes a main unit 16 and a cuff 2 connected to the main unit 16. The cuff 2 incorporates a pressure sensitive sensor 2B for detecting a pressure from the artery when wound around an arm of a patient or the like. The main unit 16 includes: a control portion 20 incorporating a CPU (central processing unit) or the like for centrally controlling and managing the blood pressure monitor 1; a pressurizing pump 21 for pressurizing the cuff 2; a blood pressure value computing portion 22 for executing a predetermined computation on a blood pressure value which is a result of measurement to calculate a maximum blood pressure, a minimum blood pressure, a pulse rate and the like; a display 23 for displaying various kinds of information; an operation input portion 24 to be operated for inputting various kinds of information; a memory portion 25 for storing programs, data and the like; a timer 26; a card R(read)/W(write) portion 27 to which the memory card 15 is detachably mounted, for reading and writing information with respect to the mounted memory card 15; an external I/F (interface) portion 28 implemented by USB or the like, for connecting an external terminal such as mobile 3; a buttery portion 29 for supplying power for driving; a sound output portion 30 for outputting sounds; and a housing portion 31. Components 21–30 are connected to the control portion 20, and the control portion 20 controls each portion connected thereto.

Figure 3:
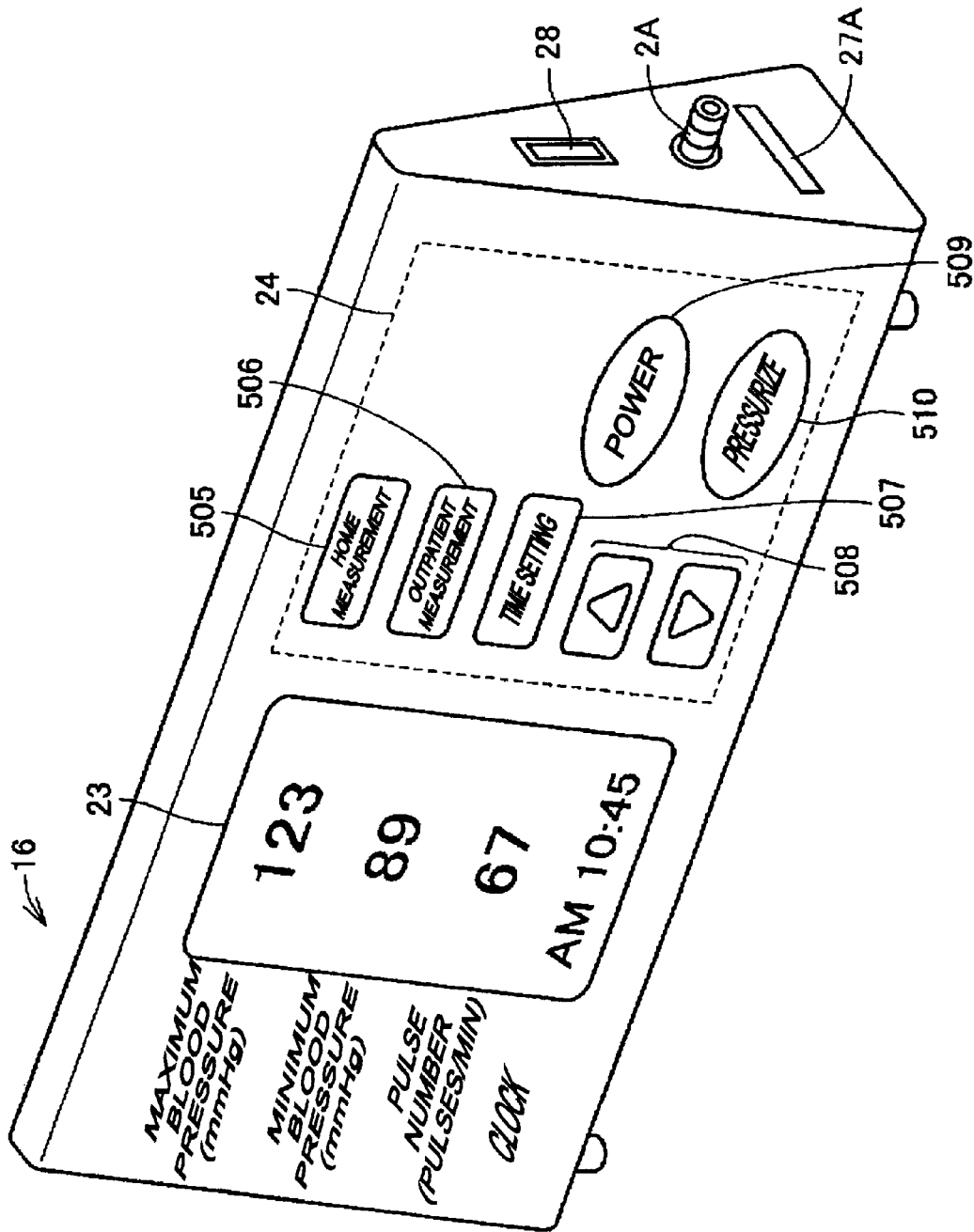
FIG. 3 is a schematic view showing a part where a patient can operate provided in a main unit of the blood pressure monitor of the invention.

FIG. 3 shows a schematic view of a part provided in the main unit 16 of the blood pressure monitor 1 which a patient can operate. In the main unit 16 of FIG. 3, as a part to be operated by a patient, the operation input portion 24 is illustrated together with the display 23. The display 23 shows a maximum blood pressure, a minimum blood pressure, a pulse, a current time and the like. The operation input portion 24 includes a button 505 to be operated when the blood pressure measurement is performed at home, a button 506 to be operated when the measurement is performed at the medical facility 7, a button 507 to be operated for setting a time, a button 508 to be touched for manipulating input data, a button 509 to be operated for turning ON/OFF the source of the monitor 1, and a button 510 to be operated for starting the pressurizing operation by the pressurizing pump 21 for starting a blood pressure measurement.

As is illustrated, on the side surface of the main unit 16 are attached the external I/F 28, a cuff connecting portion 2A to which the cuff 2 is to be connected, and a card inserting portion 27A provided in association with the card R/W portion 27.

Figure 4:
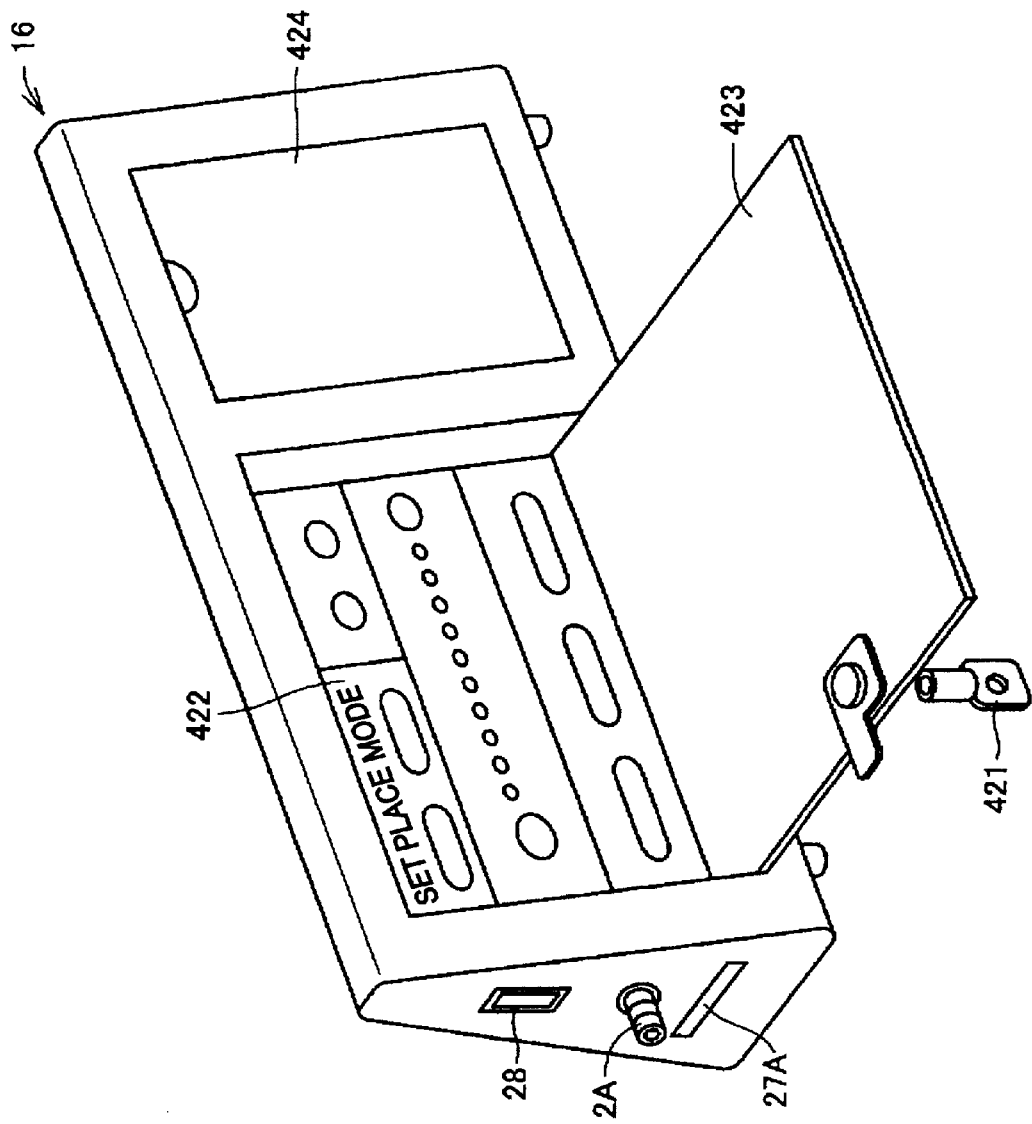
FIG. 4 shows a panel on the back surface of the main unit of FIG. 3.

As shown in FIG. 4, on the back surface of the main unit 16 is provided a panel 422 which is accessible only to a person with the authority to diagnose the subject, as well as a buttery case cover 424 in association with the buttery portion 29. The panel 422 is usually closed by a panel cover 423, but when a patient brings the blood pressure monitor 1 to the medical facility 7 and a person with the authority to diagnose the patient opens the same with a special key 421 possessed individually, the panel cover 423 is opened, thereby making the panel 422 operable.

Figure 5:
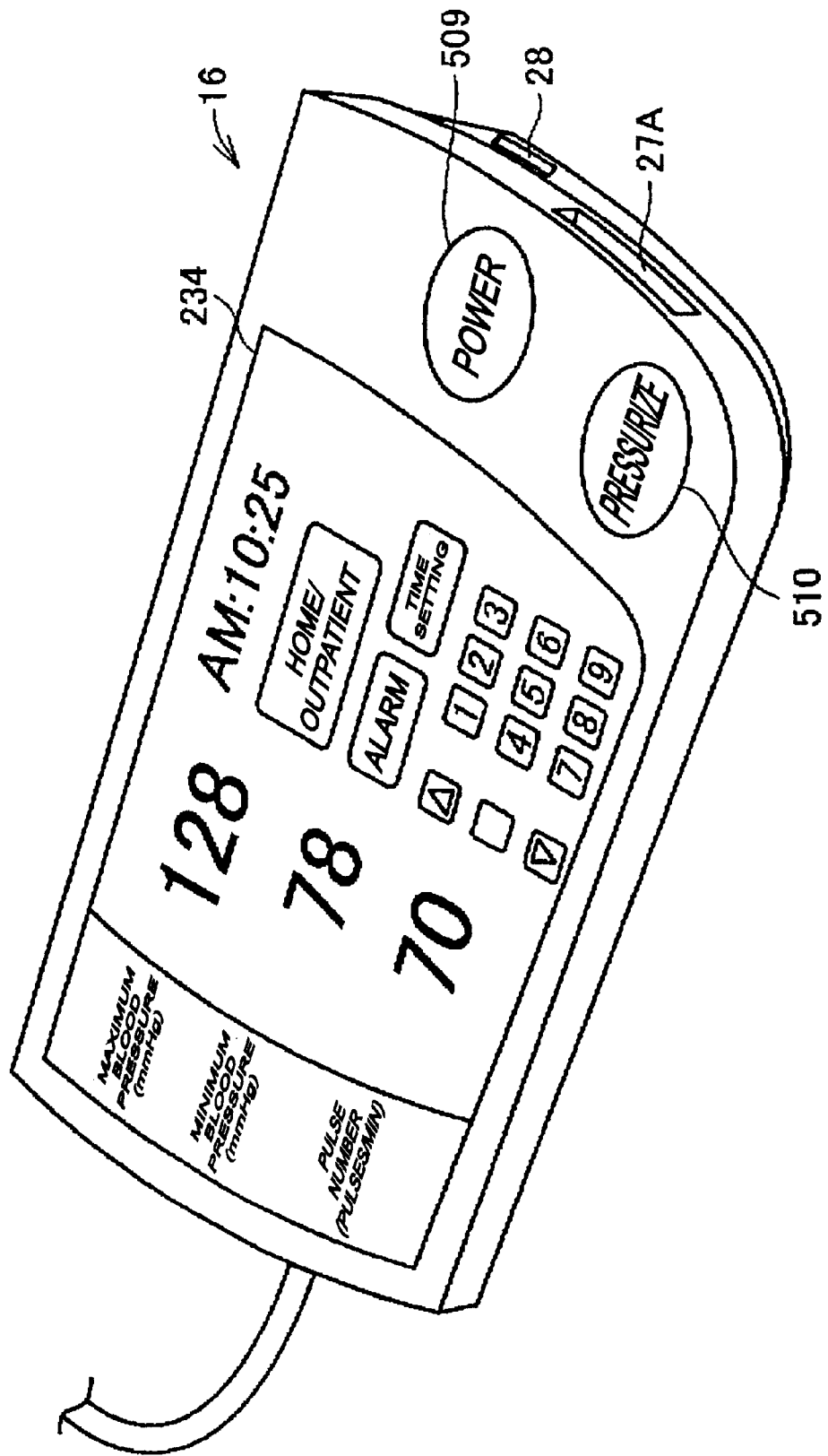
FIG. 5 shows another blood pressure monitor of the embodiments.

FIG. 5 shows the outside appearance of the main unit 16 of another blood pressure monitor 1 of the first embodiment, and in this drawing, a touch panel type display 234 wherein the display 23 and the operation input portion 24 are provided in an integrated manner. The touch panel type display 234 is usually provided for a patient, however, when the blood pressure monitor 1 is brought to the medical facility 7, and a person with the authority to diagnose the patient enters a password which is previously registered with a numerical keypad of the touch panel type display 234, the touch panel type display 234 can be switched to the screen which is exclusive for the person with the authority to diagnose the patient.

In the manner as described above, in the blood pressure monitor 1, the part where a patient operates and the part where a person with the authority to diagnose the patient makes settings or operates are separated from each other by a partition or a panel cover 423 with the key 421, or by providing a password which is specific for the person with the authority to diagnose the patient, with the result that instructions for measurement made by the person with the authority to diagnose the patient can be inputted safely and reliably and unintended modifications (for example made by a third party) can be prevented.

Figure 6:
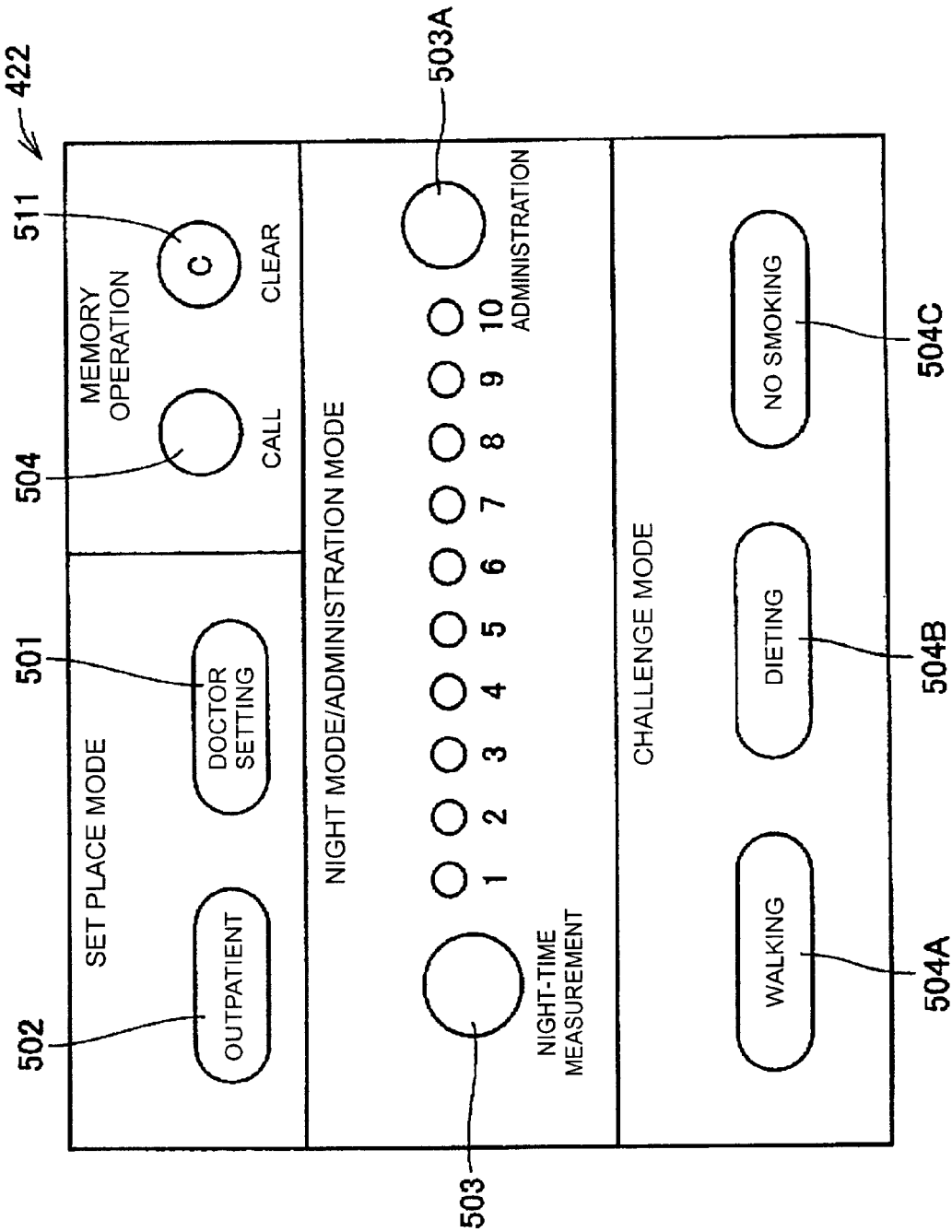
FIG. 6 shows an example of the panel of FIG. 4.

FIG. 6 is a view showing an example of the panel 422 illustrated in FIG. 4. As illustrated, the panel 422 is provided with a button 501 to be operated by a person with the authority to diagnose the patient of the medical facility 7 for setting information, a button 502 to be operated for setting information during an outpatient consultation at the medical facility 7, a button 503 to be operated for designating night-time measurements of blood pressure, a button 503A to be operated for performing measurement of blood pressure in consideration of administration of medicine, buttons 504A, 504B and 504C to be operated in accordance with life therapies for the patient, a button 504 to be operated for calling information such as blood pressure measurement data stored in the memory, and a button 511 to be operated for clearing stored information.

FIG. 7 shows an example of contents of the blood pressure measurement file 40 used in the first embodiment as well as the other embodiments. The blood pressure measurement data file 40 is written into the memory portion 25 of the blood pressure monitor 1, as well as written into the memory card 15 for storage when such memory card 15 is mounted on the card R/W portion 27 and is ready for data writing.

Referring to FIG. 7, the blood pressure measurement data file 40 includes a basic data group D1, an event data group D2, a measurement data group D3, an analysis and judgment result data group D4 and a special event data group D5. The basic data group D1 includes a terminal identification code D11 for uniquely identifying a corresponding blood pressure monitor 1, a patient code D12 for uniquely identifying a patient corresponding to the blood pressure monitor 1, a medical facility code D13 and a doctor code D14 for identifying a medical facility and a person with the authority to diagnose the patient which are permitted to process the pressure measurement data file 40, a pass word D15 for authenticating a person with the authority to diagnose the patient, and a patient record No. code D16 assigned to the corresponding patient record data file 10.

The event data group D2 includes a measurement instruction data group defining contents of measurement instructions by a person with the authority to diagnose the patient and a challenge setting data group defining life therapies. The measurement instruction data group includes data D21 instructing measurement of white-coat hypertension, data D22 instructing measurement concerning dipper, and data D23 instructing measurement of morning surge. The challenge setting data includes data D24 to D26 representing no smoking, dieting and walking. Each of the data D21 to D26 is set at "1" when a measurement instruction is made or a life therapy is set, while being set at "0" when such an instruction is not made.

The measurement data group D3 includes measurement data D3i (i=1, 2, 3, . . . , n) which is acquired every time a blood pressure measurement is performed. The measurement data D3i includes data of day and hour (minute) of blood pressure measurement, data of measured maximum blood pressure and minimum blood pressure, data of pulse and data for identifying the place of measurement (at home or as an outpatient at the medical facility 7). The data of place is referred for diagnosing the white-coat hypertension. The analysis and judgment result data group D4 and the special event data group D5 will be described later.

Figure 8:
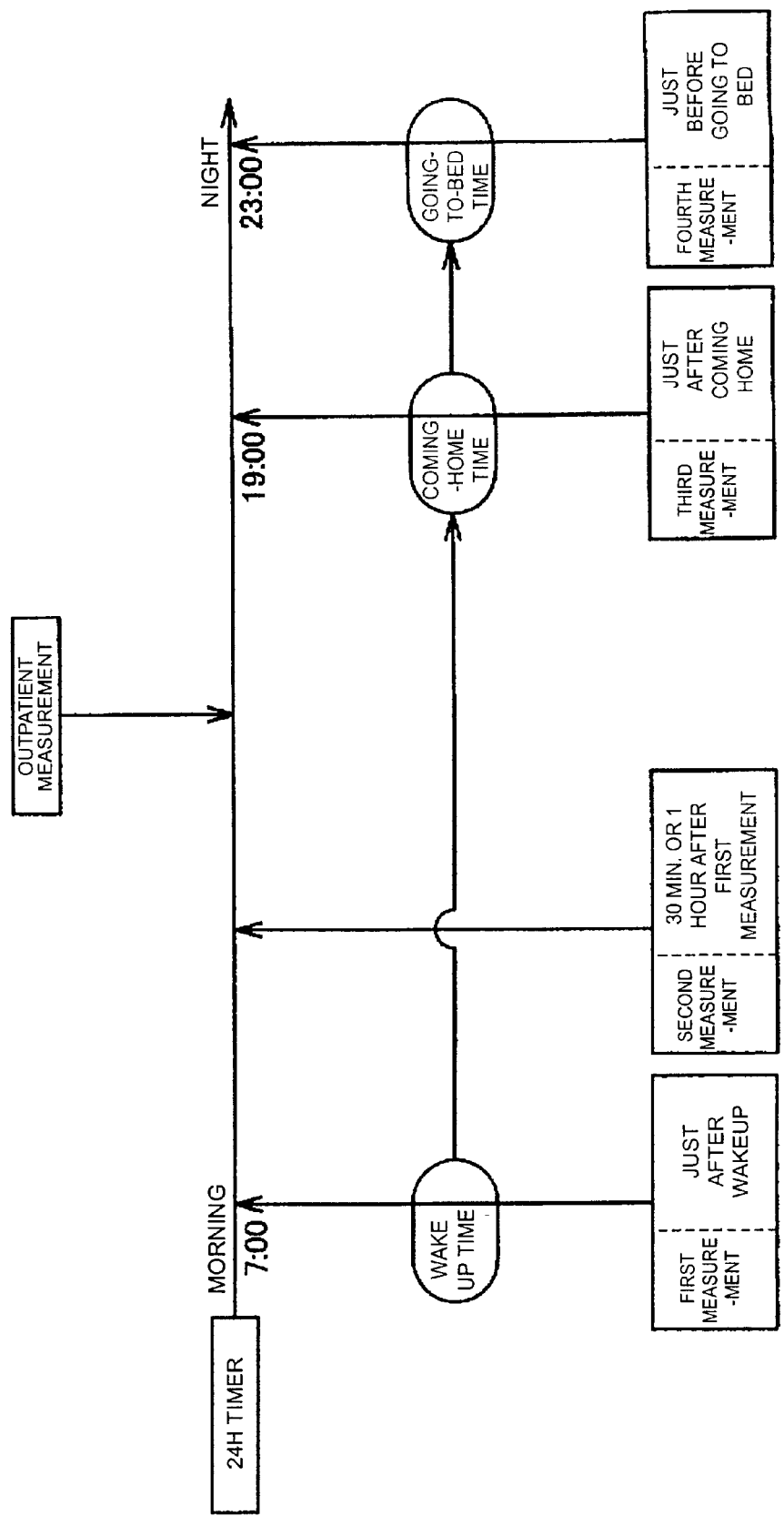
FIG. 8 shows an example of timings of the blood pressure measurements used in certain embodiments of the invention.
Figure 9:
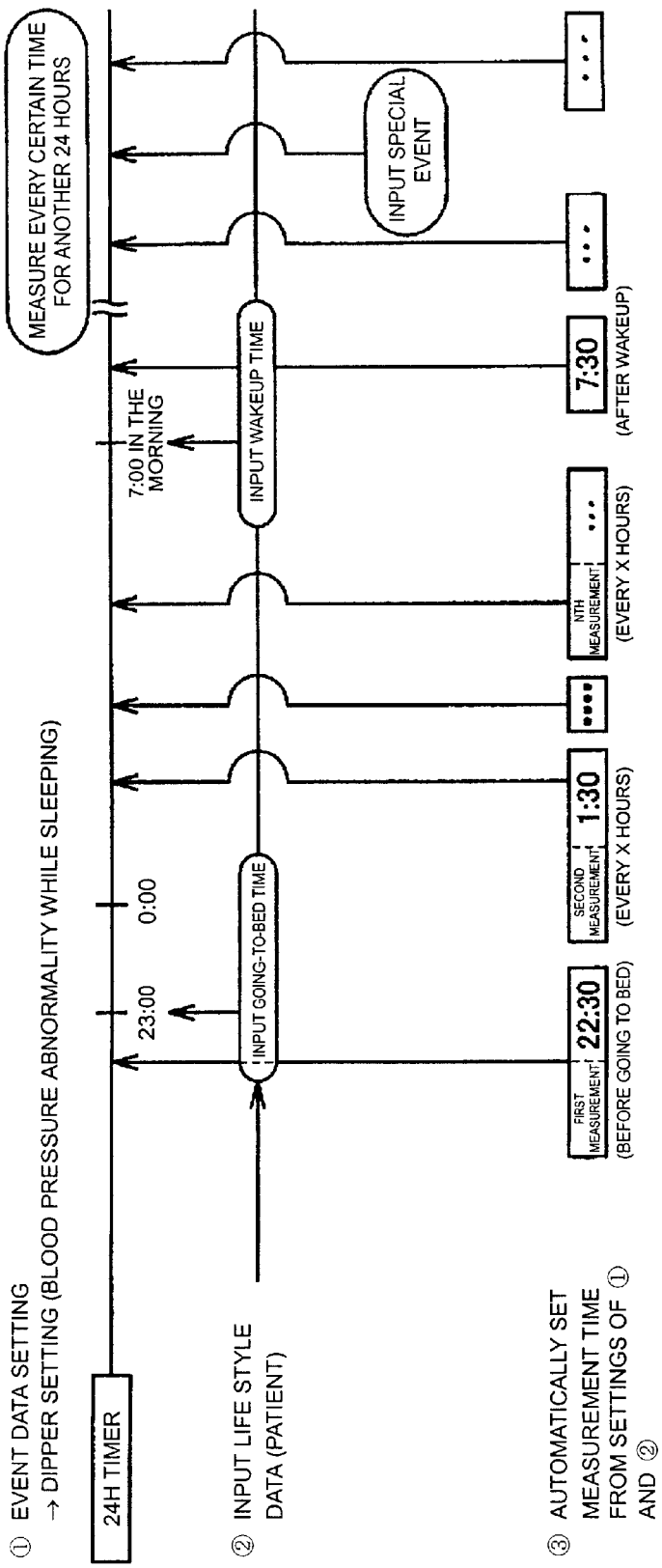
FIG. 9 shows another example of timings of the blood pressure measurements used in the invention.
Figure 11:
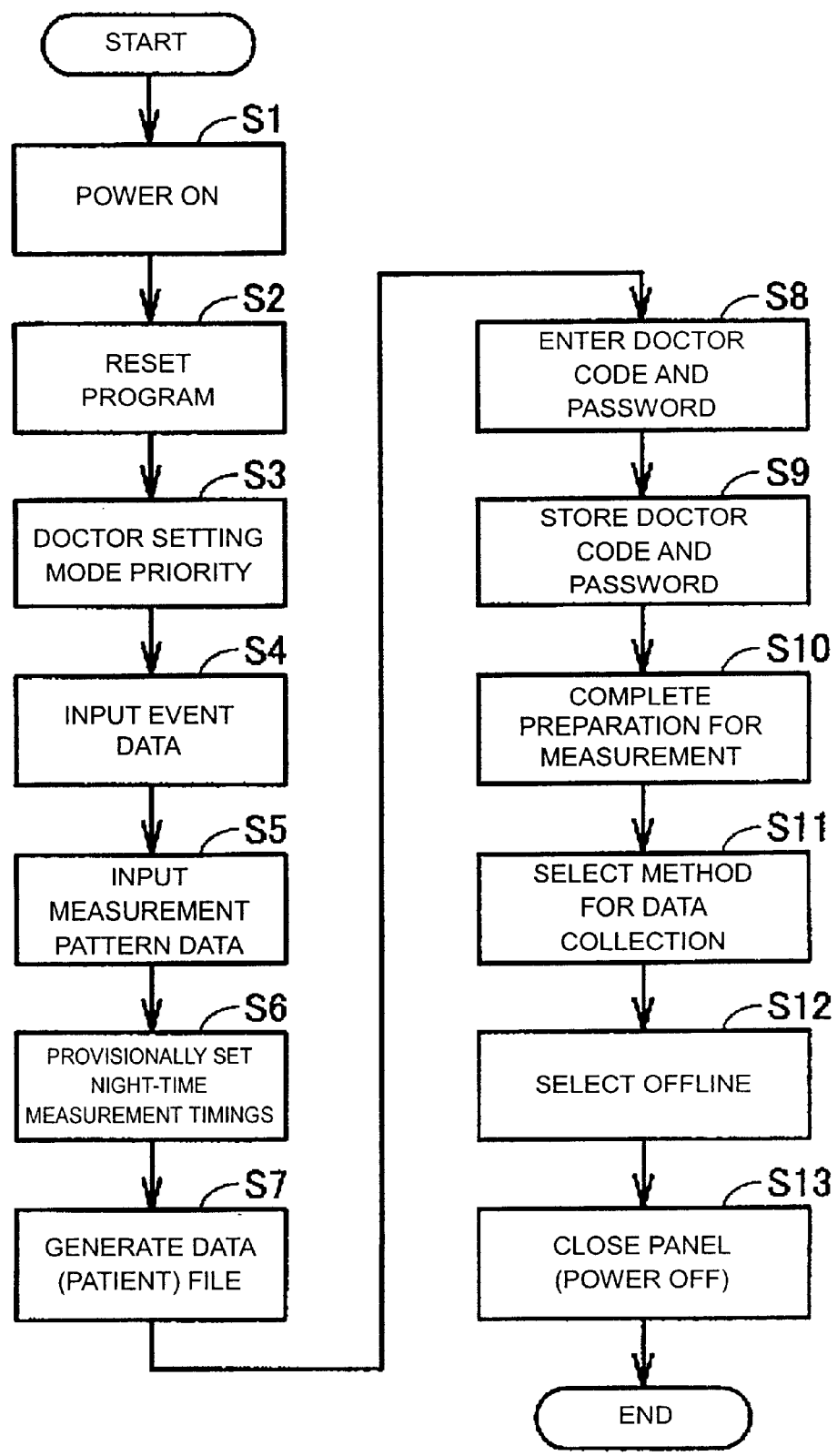
FIG. 11 is a flowchart of the initial data entry by a person with diagnostic authority according to the first embodiment.
Figure 12:
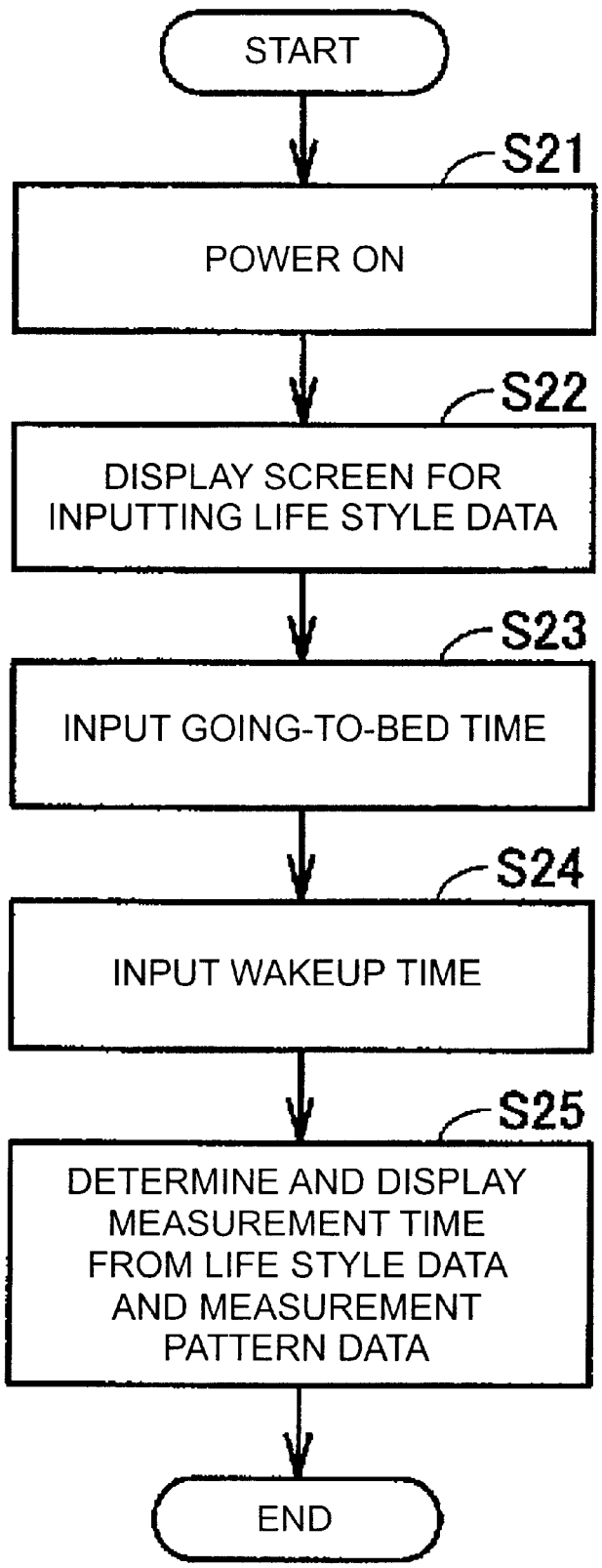
FIG. 12 is a flow chart of the life habit data entry by a patient according to the first embodiment.
Figure 13:
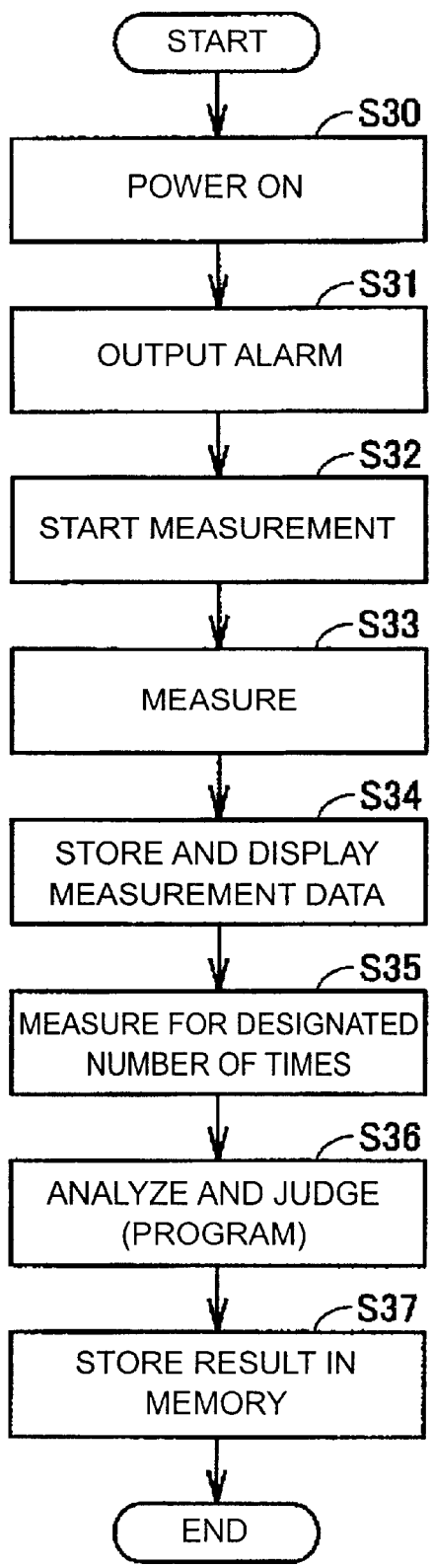
FIG. 13 is a flow chart of the blood pressure measurement according to the first embodiment.
Figure 14:
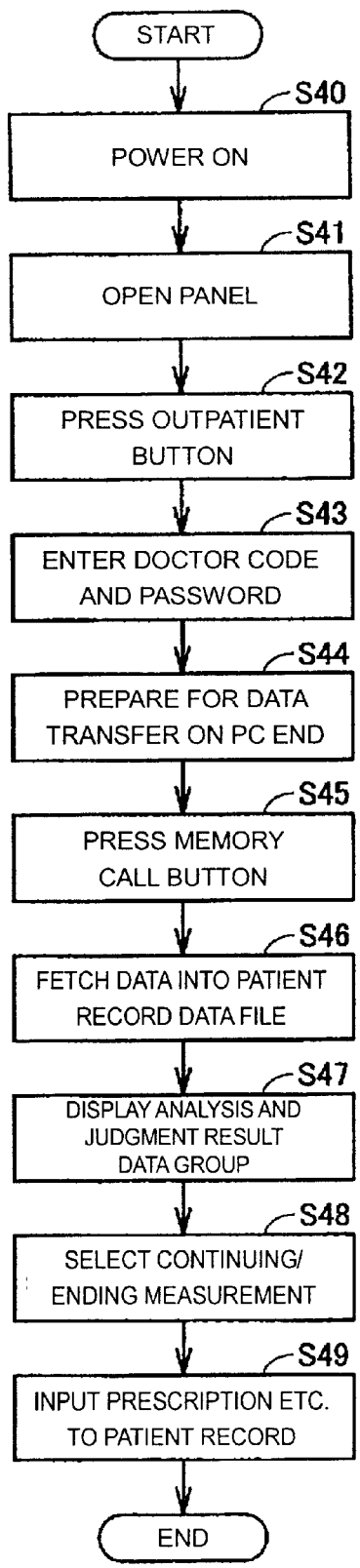
FIG. 14 is a flow chart of the data retrieval by the person with diagnostic authority according to the first embodiment.

FIGS. 8 and 9 show examples of settings of blood pressure measurement times using the blood pressure monitor 1. As a setting example of blood pressure measurement time, explanation will be made for the case where a patient works and a blood pressure measurement should be performed 4 times a day when the patient is awake.

First, at the medical facility 7, a person with the authority to diagnose the patient sets a blood pressure measurement pattern which is suited for the patient: 4 times a day when the patient is awake in this case. More specifically, the person with the authority to diagnose the patient opens the panel cover 423 of the blood pressure monitor 1 as shown in FIG. 4 to be used for blood pressure measurement or, in the case of the apparatus as shown in FIG. 5, enters a password specific to the person with the authority to diagnose the patient to thereby display a screen for the person with the authority to diagnose the patient to make settings as shown, for example, in FIG. 6. Then the person with the authority to diagnose the patient presses the button 501 to make a setting and inputs pattern data defining a plurality of timings of blood pressure measurement for the patient (4 times a day when the patient is awake). Next, the patient operates the operation input portion 24 of the blood pressure monitor 1 (operates the buttons 507 and 508) and inputs time information indicating a daily habit pattern of the patient such as going-to-bed time and wakeup time which will influence blood pressure measurements (hereinafter, referred to as life style data).

The control portion 20 variably adjusts the pattern data of blood pressure measurement according to the life style data thus inputted, calculates times when blood pressure measurements should be performed in a day, and stores the setting in the memory portion 25 or the like. Since clocking is executed by the timer 26, the control portion 20 controls the sound output portion 30 to output alarm sounds such as light melodies or buzzer sounds or controls the display 23 to blink the legend of "alarm" at every blood pressure measurement time set in the memory portion 25, for example 5 minutes before every blood pressure measurement time, for urging the patient to perform a blood pressure measurement.

Next, the details of the variable adjustment of pattern data of blood pressure measurement based on the life style data by the control portion 20 as described above will be explained. Once life style data of the patient is inputted and a daily wakeup time is set, a setting is made so that a first blood pressure measurement is performed directly after the patient wakes up. And next, a setting is made so that a second blood pressure measurement is performed after the first measurement and before the patient starts his or her activities that day. This second measurement depends on the life style data of the patient and is generally performed 30 minutes to 1 hour after the first measurement and at least before going out for work, though the patient may have breakfast between the first and the second blood pressure measurements. In the case where the life style data of the patient according to this embodiment indicates that the patient goes out for work 1 hour after wakeup, a setting is made so that the second measurement is performed 45 minutes after the first measurement. Next, on the basis of the life style data, a setting is made so that a third measurement is performed when the patient comes home and hence still has physical and mental stresses left over from work, and a fourth measurement is performed just before the patient goes to bed, preferably at least 30 minutes before going to bed when the patient has finished the activities of that day. Preferably, such measurements are continuously performed for 4 days or more including a day-off over 2 weeks or more, in order to achieve an accurate diagnosis. A chart of the timings automatically set in this manner is shown in FIG. 8. When a measuring time arrives, the patient confirms that the button 505 representing "home measurement" in FIG. 3 is in the ON condition and starts a blood pressure measurement.

It is to be noted that the number of times of blood pressure measurements, for example one measurement or three measurements for averaging the measurements, may be set by the person with an authority to diagnose the patient to operate the button 501.

In the case where the patient goes to the medical facility 7 and undergoes a blood presser measurement during the above period of blood pressure measurement, the measurement of blood pressure is performed by pressing the button 506 representing "outpatient measurement". The timing chart of FIG. 8 shows a case in which an outpatient measurement is performed between the second and the third blood pressure measurements. Though not being illustrated, it is also possible to configure the system so that whether the measurement is performed in the presence of a person with the authority to diagnose the patient or in the absence of a person with the authority to diagnose the patient such as at a waiting room may be made distinguishable.

In this manner, when the button 505 or 506 is operated and thus in the ON condition, data corresponding to the button in the ON condition is registered in correspondence with the place data of the measurement data D3i.

Although the blood pressure measurements are performed when the patient is awake in the above example, blood pressure measurements may be performed when the patient is asleep. Specifically, the person with the authority to diagnose the patient inputs a blood pressure measurement pattern defining timings of blood pressure measurement by pressing the button 503 together with the button 501 so that the patient goes to bed while wearing the cuff 2 on the arm after performing a measurement before going to bed, and a measurement is performed every certain period of time, for example, every 30 minutes or every 2 hours. This can be achieved by operating input buttons 1 to 10 in the case of the panel 422 of FIG. 6, or the input buttons of the numerical keypad in the case of FIG. 5. In this manner, a blood pressure measurement pattern when the patient is asleep is set by the person with the authority to diagnose the patient, and the blood pressure measurement pattern thus set is registered in the memory portion 25, whereby a blood pressure is automatically measured every period of time that is set by the person with the authority to diagnose the patient by means of the cuff 2 worn on the arm even when the patient is asleep.

Furthermore, the control portion 20 may identify the blood pressure measurement pattern according to the contents of the measurement instruction data of the event data group D2 set by the person with the authority to diagnose the patient, variably adjust the identified blood pressure measurement pattern based on the life style data of the patient and determine a plurality of timings of blood pressure measurements. Specifically, when the data D22 (dipper setting) of the event data group D2 is set at "1" for the person with the authority to diagnose the patient to diagnose an abnormality of blood pressure when the patient is asleep, the control portion 20 identifies a blood pressure pattern based on the data 22, variably adjusts the identified blood pressure pattern in accordance with the life style data of the patient, and determines a plurality of timings of blood pressure measurements, for example, as shown in FIG. 9.

In this case, the blood pressure measurement pattern may differ between when the patient is asleep and when the patient is awake, however, the setting may be made so that the measurement is performed every certain time in an interval as the same as that of the measurements when the patient is asleep, all day over 24 hours. When some events that will influence the blood pressure measurements such as exercise, driving, meals, smoking or drinking occur in daily life, the patient may input the event by operating the button of FIG. 6. The inputted event is sequentially registered in the special event data group D5 of the pressure measurement data file 40 chronologically in accordance with the timing when the event is inputted.

Furthermore, the person with the authority to diagnose the patient operates the button 503A in FIG. 6 to enable recognition and storage of presence/absence of administration of medicine and kinds of medicine by means of the corresponding input buttons 1 to 10. When information indicating presence/absence of administration of medicine and kinds of medicine under administration is inputted, the information is sequentially registered in the special event data group D5 of the blood pressure measurement data file 40. Furthermore, as buttons for the "challenge mode" which denote life therapies (improvement of life style), buttons 504A to 504C of "no smoking", "dieting" and "walking" are provided, and by operating the respective buttons corresponding to the life therapies challenged according to the instruction by a person with the authority to diagnose the patient or the patient's own intent, such information can be stored as data D24 to D26 of the blood pressure measurement data. In this case, three life improving events by life therapies are presented, however, the events are not limited to the above.

As described above, in the blood pressure measurement data file 40, the basic data group D1 which is initially set, the event data group D2 to be set by the person with the authority to diagnose the patient in accordance with the circumstances of the patient, the measurement data group D3i obtained by blood pressure measurements at the measurement times shown in FIGS. 8 and 9, for example, and the special event data group D5 are stored.

The blood pressure monitor 1 according to this embodiment assists a hypertension diagnosis of a patient by a person with the authority to diagnose the patient by performing an analysis such as comparing and inspecting the measurement data D3i of the measurement data group D3 obtained by performing blood pressure measurements in timings set as described above in accordance with a predetermined procedure, and registering the analysis and judgment result data group D4 indicating results of the analysis and judgment in the blood pressure measurement data file 40 for presentation to the person with the authority to diagnose the patient. In this context, a diagnosis of hypertension is just an example and target symptoms to be diagnosed are not limited to this. One example of an analysis and judgment procedure for hypertension diagnosis according to this embodiment is shown in FIG. 10 in a tabular manner. This analysis procedure is implemented by the CPU of the control portion 20 executing an analysis and judgment program previously stored in the memory portion 25. Herein a maximum blood pressure value is used as a blood pressure measurement data (blood pressure value) for the analysis.

Referring to FIG. 10, a first blood pressure measurement data directly after wakeup (A) and a second blood pressure measurement data (B) are compared, and if B/A is a certain value or more, in this case 130% or more, "MS" is outputted. This output operation writes the result into the analysis and judgment result data group D4 of the blood pressure measurement data file 40 or to display it on the display 23. "MS" means a rapid rise of blood pressure in the morning (so-called morning surge) which is considered to be a precursor of cardiovascular accidents such as acute myocardial infarction.

Next, an average blood pressure value of 24 hours and a blood pressure value measured in day-time are compared. In the measurement pattern shown in FIG. 8, a value of the fourth measurement just before going to bed or an average value of the first measurement just after waking up and the fourth measurement just before going to bed is employed as an average blood pressure value of 24 hours (C), and measurement data of the third measurement directly after coming home is employed as a blood pressure value of a day-time measurement (D). As a result of comparison of C and D, if the value of D/C is less than 100%, for example, "in-D" (which means an inverted dipper, and considered as a patient who is likely to have organ damage since the blood pressure higher in the night-time than in the day-time or the 24 hour average) is outputted; if D/C is not less than 100% and not more than 110%, "non-D" (which means a non-dipper indicating that the increase in day-time blood pressure is slight with respect to night-time blood pressure) is outputted; if D/C is not less than 110% and not more than 120%, "D" (which means a dipper, indicating that a decrease in night-time blood pressure is normal) is outputted; and if the D/C is more than 120%, "ex-D" (which means an extreme dipper, indicating that the decrease is excessive) is outputted.

In the case of the blood pressure measurement according to the timing chart as shown in FIG. 9, a computation is performed in the same manner as the measurement pattern of FIG. 8 while considering an average of blood pressure values when the patient is asleep as a night-time blood pressure value (C') and an average of blood pressure values measured when the patient is asleep excluding the measurement data from just after waking up and the measurement data from just before going to bed as a day-time blood pressure value (D), and a result is outputted.

Additionally, the patient brings the blood pressure monitor 1 at the time of going to the medical facility 7, and a specific value (E) measured when the patient is at the medical facility 7, in particular, a blood pressure value (E) measured in front of a person with the authority to diagnose the patient is compared with an average (D) of measurement data when the patient is awake excluding a blood pressure value measured just after waking up and a blood pressure value measured just before going to bed. If E/D is a certain value or more, for example, 120% or more in this case, "WH" (which means "white-coat hypertension") is outputted. Alternative to the average (D) of measurement data when the patient is awake excluding a blood pressure value measured just after waking up and a blood pressure value measured just before going to bed, a blood pressure value (D) measured just after coming home, or any blood pressure values (D) measured when the patient is awake excluding just after waking up and just before going to bed may be employed. It goes without saying that a blood pressure monitor provided at a hospital may be used rather than the patient's blood pressure monitor 1.

Furthermore, among the functions of analysis and judgment for the blood pressure data, monitoring of blood pressure after administration of medicine and monitoring of blood pressure during conducting a life therapy (improvement of life style) as a challenge mode are possible. That is, kinds of medicine are recognized, and a starting day of administration can be inputted with the button 503A and the keys 1 to 10 of FIG. 6. First, a blood pressure value (A), a blood pressure value (B) measured 30 minutes after waking up, B/A before or during administration (represented by "m"), and A, B, B/A of predetermined days or a predetermined period from m (represented by "n") are recorded, A, B, B/A are compared between m and n, and the increase/decrease thereof is outputted by % or the like, thereby checking the effect of the administration and the life therapy (improvement of life style).

The % values to be used for these analyses and judgments are set in accordance with the kinds of hypertension which are objects of the diagnosis, and these values may be appropriately changed via the panel 422 according to the judgment by a person with the authority to diagnose the patient. Also the blood pressure values are selectively read out from the measurement data D3i and the computation formula for these selectively readout blood pressure values may be set in accordance with the type of hypertension which is to be diagnosed.

Furthermore, by referring the special event data group D5 (exercise, driving, meals, smoking, drinking and the like) recorded in the blood pressure measurement data file 40, it is possible to grasp the relationship between these special events and the measured blood pressure data and the results of analysis and judgment.

FIGS. 11 to 14 are flowcharts showing a series of procedures as described above. Referring to these flowcharts, operations of the blood pressure data processing system according to the first embodiment will be explained.

A patient visiting the medical facility 7 consults a person with the authority to diagnose the patient, and the person with the authority to diagnose the patient determines pattern data and event data for blood pressure measurement in order to diagnose hypertension in the patient based on the result of the consultation, and turns ON the power by pressing the button 509 of the blood pressure monitor 1 (step S1, hereinafter step is abbreviated as simply "S"). As a result of this, an initial setting such as program reset is executed in the blood pressure monitor 1 (S2). The person with the authority to diagnose the patient opens the panel cover 423 with the key 421 and presses the button 501 in the panel 422 which is provided for a person with the authority to diagnose the patient to make a setting, and accordingly the blood pressure monitor 1 is ready to receive instructions by the person with the authority (S3). In this mode, the screen for patient is not displayed. The person with the authority to diagnose the patient selects, for example, a dipper measurement in selecting an event, and accordingly the data D22 of dipper classification selected in the event data group D2 is set at "1" (S4). Thereafter, measurement pattern data is inputted (S5). Herein, since the person with the authority to diagnose the patient presses the button 503 corresponding to night-time measurement data, timings of night-time measurements are set temporally (S6).

The person with the authority to diagnose the patient confirms medical record data written in a patient record, and inputs a patient record No., a patient code and the like, and based on such inputted data, a blood pressure measurement data file 40 for that patient is generated and written into the memory portion 25. The blood pressure measurement data file 40 may be generated at the personal computer 12 and transferred to the blood pressure monitor 1 via a cable to be written into the memory portion 25, or may be transferred online over the network 5.

As the blood pressure measurement data file 40 is generated, the person with authority to diagnose the patient enters a doctor code and a password (S8) which are then stored in the basic data group D1 of the generated blood pressure measurement data file 40 (S9), to complete preparation for the pressure measurements (S10). Thereafter, a method for collecting data is selectively set (S11). In this case, an assumption is made that offline selection of data collection is executed by the transferring method (1) as shown in FIG. 1A (S12). Therefore, the measurement data D3i and the like will be written into the blood pressure measurement file 40 set in the memory portion 25. Afterwards the person with the authority to diagnose the patient closes the panel 422 with the panel cover 423, locks with the key 421, and turns OFF the power by operating the button 509 (S13).

Then the blood pressure monitor 1 is handed to the patient, the person with the authority to diagnose the patient explains to him/her about blood pressure measurement at home, and the patient starts the blood pressure measurement at home.

As shown in FIGS. 3 and 4, since the patient is not allowed to operate the panel 422 to be operated by the person with the authority to diagnose the patient, the contents that are inputted by the person with the authority to diagnose the patient by operating the panel 422 will not be changed by the patient, which secures proper measurement and diagnosis.

In measuring a blood pressure at home using the blood pressure monitor 1, the patient turns the power on by operating the button 509 (S21) to cause the display 23 to display an input screen for life style data (S22). Referring to this screen, the patient inputs a time of going to bed (S23). Concretely, the patient operates the button 508 while monitoring the time being displayed in the display 23, and when a desired time of going to bed is displayed, the time setting button 507 is pressed to input the time of going to bed.

Subsequently, also a time of waking up is inputted in the same manner (S24). In this case, only the time of going to bed and the time of waking up are inputted, however, various time data determining the specific life style of the patient such as time of coming home and time of going to work may be inputted.

In the manner as described above, the control portion 20 variably adjusts the timing represented by the measurement pattern data inputted by the person with the authority to diagnose the patient at the medical facility 7 to determine a plurality of timings for measuring blood pressure on the basis of the inputted life style data, and stores them in the memory portion 25 as well as displays them on the display 23 (S25).

Once the measurement times have been automatically set in the manner as described above, the patient prepares for blood pressure measurement.

Upon turning ON the power by operation of the button 509 of the blood pressure monitor 1 (S30), clocking is executed by the timer 26, and when the time reaches the first measurement time set in the memory portion 25 or 5 minutes before the first measurement time, an alarm is outputted as described above (S21). Then the patient confirms the outputted alarm and starts a blood pressure measurement. Concretely, the patient winds the cuff 2 around the arm, presses the button 510 of the blood pressure monitor 1, thereby starting the blood pressure measurement (S32). A blood pressure is measured in this manner (S33), and a result of the blood pressure measurement is displayed in the display 23 together with a numerical table. A maximum blood pressure, a minimum blood pressure and a pulse number obtained in the measurement are also recorded in the measurement data file 40 of the memory portion 25 as the measurement data D3i together with the measurement time (S34). At this time, "at home" is recorded in the data representing the place in the measurement data D3i. This information is automatically recorded in response to a turning ON operation of the button 505 for an at home measurement made by the patient.

Blood pressure measurements are repeated in the manner as described above every time the set measurement times arrive, and the measurement data D3i thereof is sequentially registered in the blood pressure measurement data file 40 (S35). The analysis and judgment process as described above is then executed in accordance with the program for analysis and judgment stored in the memory portion 25, and the result is written into the analysis and judgment data group D4 of the blood pressure measurement data file 40 (S36, S37).

In this way, the blood pressure measurements at home by the patient and the analysis and judgment end.

Later, the patient brings the blood pressure monitor 1 to the medical facility 7, and consults a person with the authority to diagnose the patient. The person with the authority to diagnose the patient receives the blood pressure monitor 1 presented by the patient, connects the blood pressure monitor 1 with the personal computer 12 via the cable as shown in the data transferring method (1) of FIG. 1A, presses the button 509 of the blood pressure monitor 1 to turn ON the power (S40). Thereafter, the person with the authority to diagnose the patient opens the panel cover 423 using the key 421, making the panel 422 operable (S41), and presses the button 502 displaying outpatient in the panel 422 (S42). Then the person with the authority to diagnose the patient enters a doctor code and a password for requesting readout of the blood pressure measurement data file 40 by operating the keyboard of the personal computer 12 (S43).

Upon receiving the doctor code and the password, the control portion 20 of the blood pressure monitor 1 collates the received doctor code and the password with the doctor code D14 and the password D15 recorded in the blood pressure measurement data file 40 of the memory portion 25, and if it is determined that the received password and doctor code coincide with those recorded in the memory portion 25, or in other words, if the read request is verified, the control portion 20 permits readout of the blood pressure measurement data file 40, whereby preparation for data transfer of the blood pressure measurement data file 40 to the personal computer 12 completes at the personal computer 12 end (S44).

In this manner, since readout of the blood pressure measurement data file 40 is permitted only when the read request is verified, it is possible to prevent the data from being read in response to an unverified request by a third party and thus invasion of privacy of individual patients can be avoided.

Afterwards, as the person with the authority to diagnose the patient presses the call button 504 in the panel 422, the blood pressure measurement data file 40 in the memory portion 25 is written into the patient record data file 10 of the server apparatus 11 of the medical facility 7 through the personal computer 12 via the connected cable (S46). Then, the blood pressure measurement data file 40 thus read is read out from the patient record data file 10 of the server apparatus 11 to be displayed on the screen of the personal computer 12 (S47).

The person with the authority to diagnose the patient judges the presence/absence of various kinds of symptoms such as hypertension and determines a prescription with reference to the analysis and judgment result data group D4 of the display contents, and then judges whether or not continuous blood pressure measurement is required (S48). If continuous measurement is required, the button 511 of the panel 422 is not operated, whereas if it is judged to finish the blood pressure measurement, the button 511 is operated and the contents of the blood pressure measurement data file 40 in the memory portion 25 are cleared.

Since the contents of the blood pressure measurement data file 40 are displayed, the person with the authority to diagnose the patient can confirm the analysis and judgment result data group D4 based on the previously set contents such as measurement time and measurement interval required for obtaining blood pressure value information useful for diagnosis and treatment of hypertension, and useful indexes for assisting a diagnosis and treatment of hypertensions such as dipper and non-dipper.

Furthermore, by confirming the displayed special event data group D5 and challenge setting data, it is possible to derive useful indexes for diagnosing types of hypertension in association with the courses before and after administration, changes after administration, smoking and meals, and life therapies (improvement of life style) such as exercise.

Also by confirming the contents representing a place in the displayed measurement data D3i, it is possible to efficiently determine the presence/absence of "white-coat hypertension", by comparing measurement data obtained when the patient is at the medical facility and particularly with the person with the authority to diagnose the patient, and a daily measurement data.

In this manner, information such as prescriptions determined by the person with the authority to diagnose the patient while referring to the contents of the blood pressure measurement data file 40 is inputted via the keyboard 14 of the personal computer 12, and inputted to the corresponding patient record data file 10 of the server apparatus 11 (S49). Thereafter, the blood pressure monitor 1 is lent to the patient again if it is determined that continuous measurement of blood pressure is required. To the contrary, if a determination for ending the measurement is made, the blood pressure monitor 1 is collected from the patient.

The terminal identification code D11 is set for the blood pressure monitor 1, and the patient record No. code D16 is set for the blood pressure measurement data file 40. Furthermore, since the password D15 is required for reading out the data, privacy and security concerning the contents recorded in the blood pressure measurement data file are secured.

By means of the blood pressure monitor 1 having the features as described above, information for diagnosing types of hypertension (for example, judgment of dipper, non-dipper, inverted dipper and extreme dipper) and information for diagnosing the white-coat hypertension that have been difficult to perform heretofore and numerical values for determining a morning blood pressure increase (morning surge) or increased ratio with respect to the measurement before going to bed can be obtained with extreme easiness, which gives an advantage in diagnosis of hypertension to the person with the authority to diagnose the patient. Furthermore, in conventional systems, it has been impossible to determine a correlation between blood pressures measured at night and blood pressures measured early in the morning by a conventional simple blood pressure measurement and hence it has been difficult to administer proper antihypertensive medications. According to this embodiment, however, assistance of proper and efficient administration of antihypertensive medications by a person with authority to diagnose the patient becomes possible.

Figure 15:
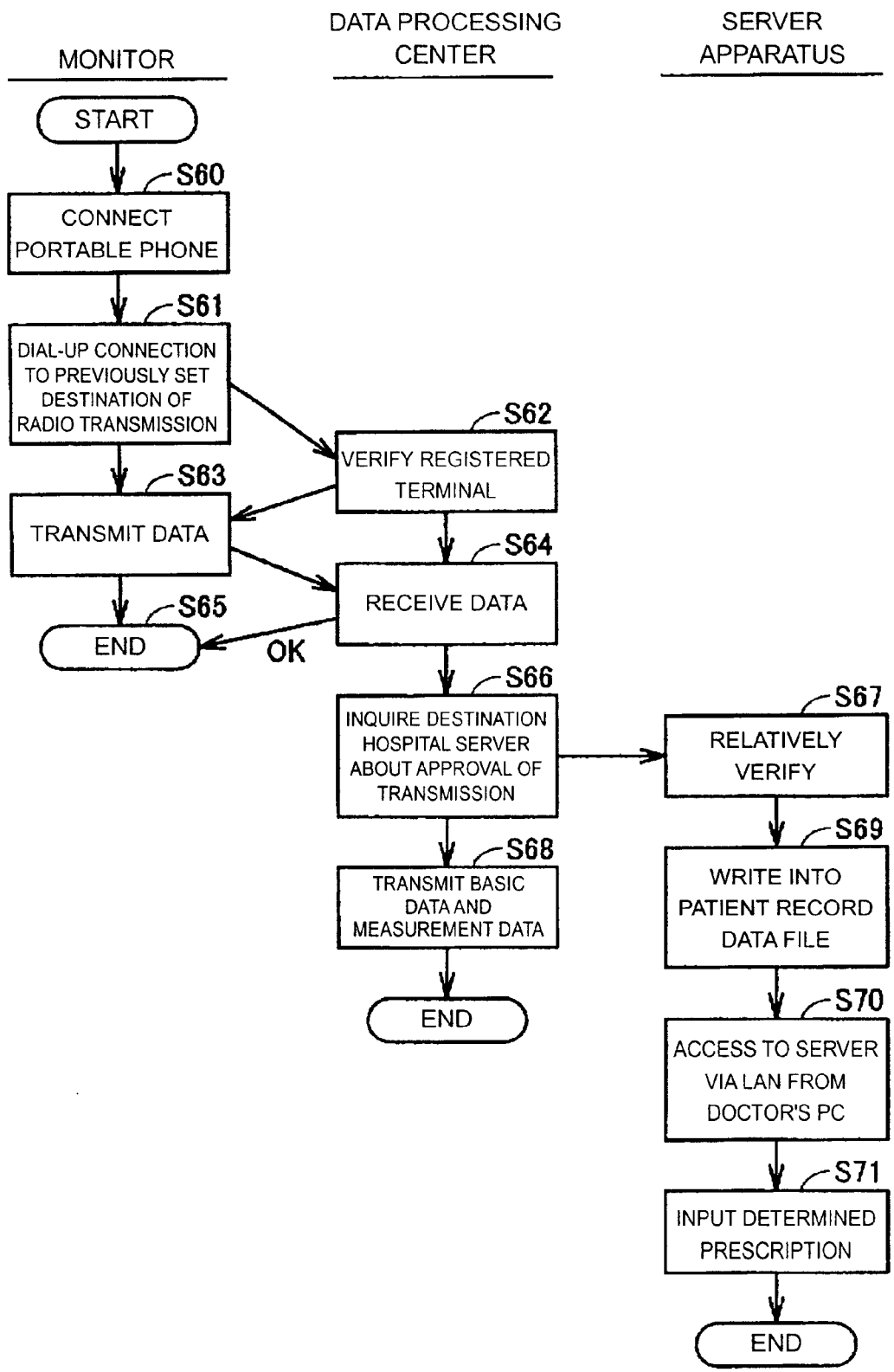
FIG. 15 is a flow chart of a blood pressure measurement data processing according to a second embodiment.

FIG. 15 is a flowchart showing a procedure of processing blood pressure measurement data according to a second embodiment of the invention. In the above-described first embodiment, the blood pressure measurement data file 40 is transferred off-line by cable connection, however, in this embodiment, online transfer via cable connection using a mobile 3 is employed. In this embodiment, only the method for data transferring is different from that of the first embodiment, and other processing procedures, functions and configuration of the apparatus are as the same as those shown in the first embodiment, the explanation of which will be omitted.

With reference to FIG. 15, as explained above, when a series of blood pressure measurements completes and the measurement data group D3, the analysis and judgment result data group D4 and the like are registered in the blood pressure measurement data file 40, the patient connects the mobile 3 such as a portable phone to the blood pressure monitor 1 via the external I/F port 28 in order to transfer the blood pressure measurement data file 40 (S60). Then, by way of dial-up connection to a radio destination, the mobile 3 becomes connected with the data processing center 6. At this time, the password D15, the patient code D12 and the terminal identification code D11 registered in the blood pressure measurement data file 40 are transmitted, and the data processing center 6 receives these data and verifies the blood pressure monitor 1 according to the received contents (S62). Notified that the blood pressure monitor 1 has been verified, the blood pressure monitor 1 transmits data of the blood measurement data file 40 (S63), the data processing center 6 receives the transmitted blood pressure measurement data file 40 (S64) and transmits a response that the reception has completed to the blood pressure monitor 1 via the mobile 3, and then the blood pressure monitor 1 having received this ends the series of processes (S65).

Thereafter, the data processing center 6 interrogates the server apparatus 11 of the medical facility 7 which is a destination of transmitting the blood pressure measurement data file 40 whether or not data transmission is approved, and verification is relatively conducted between the medical facility 7 and the server apparatus 11 (S67). This communication between the data processing center 7 and the server apparatus 11 is preferably carried out via VPN or a dedicated line for security.

Upon reception of approval data of data transmission from the server apparatus 11 of the medical facility 7, the data processing center 6 transmits the contents of the blood pressure measurement data file 40 to the server apparatus 11 (S68), and the server apparatus 11 writes the contents of the blood pressure measurement data file 40 thus received into the corresponding patient record data file 10 (S69). Afterwards the processing of the data processing center 6 ends.

The person with authority to diagnose the patient accesses to the corresponding patient record data file 10 of the server apparatus 11 via the LAN (not shown) of the medical facility 7 from the personal computer 12 (S70), makes a diagnosis with reference to the contents of the blood pressure measurement data file 40 to determine a prescription, and inputs the determined prescription by operating the keyboard 14. The inputted prescription is then recorded on the corresponding patient record data file 10 (S71).

Figure 16:
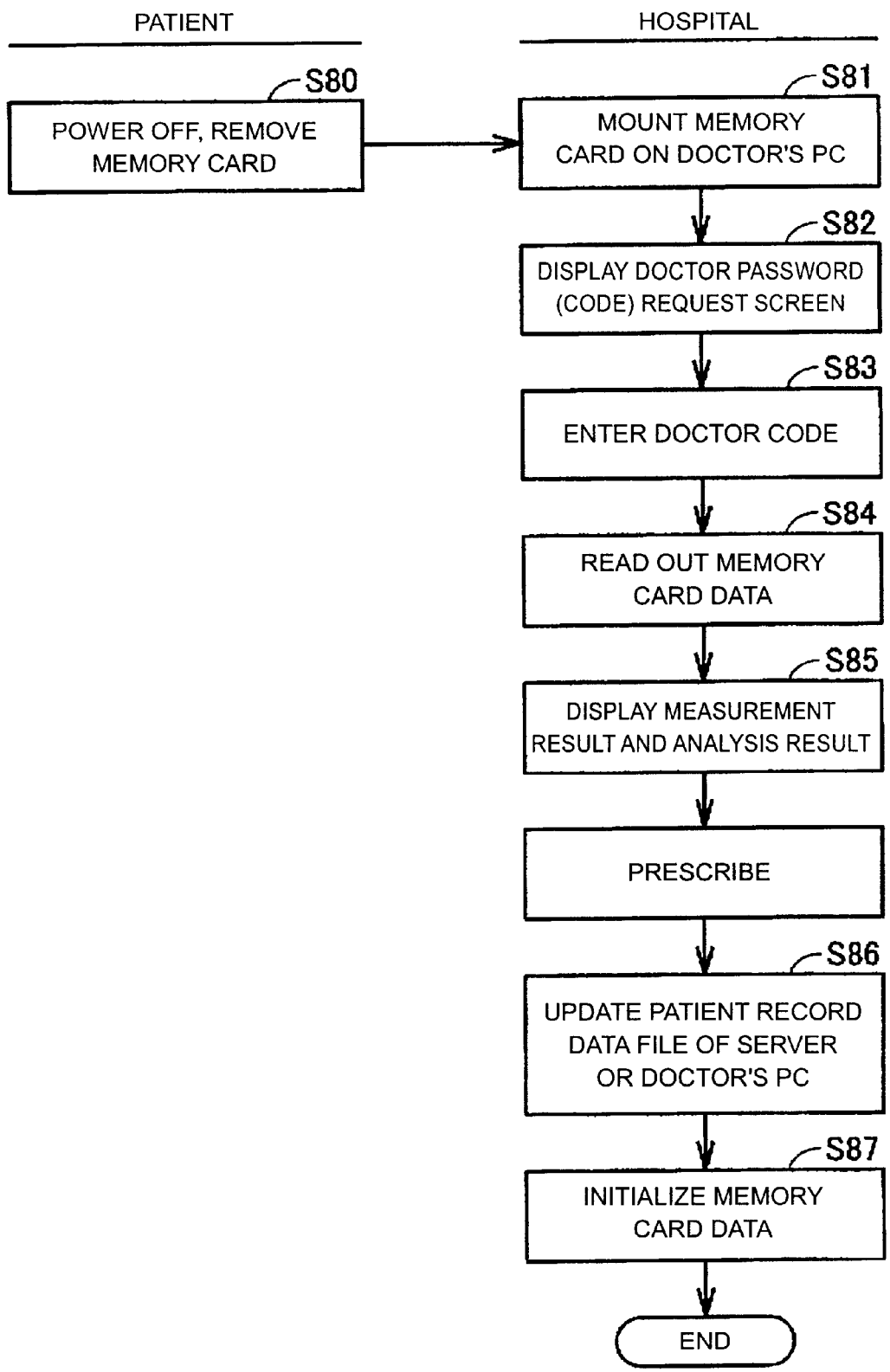
FIG. 16 is a flow chart of a blood pressure measurement data processing according to a third embodiment.

FIG. 16 is a flowchart of blood pressure measurement data processing according to a third embodiment. In this embodiment, data of the blood pressure measurement data file 40 is transferred by using the memory card 15. In this embodiment, only the method for data transferring is different from that of the first embodiment, and other processing procedures, functions and configuration of the apparatus are as the same as those shown in the first embodiment, the explanation of which will be omitted.

Referring to FIG. 16, blood pressure measurements are performed in the procedure as described above, and after completion of recording the contents of the measurement data group D3 and the like in the blood pressure measurement data file 40, as well as recording the analysis and judgment result data group D4, the memory card 15 in which the blood pressure measurement data file 40 is written is removed from the blood pressure monitor 1 and the blood pressure monitor 1 is turned OFF (S80).

The patient brings the removed memory card 15 to the medical facility 7 when coming there as an outpatient, and the person with authority to diagnose the patient mounts the memory card 15 thus brought in the memory card reader/writer 13 of the personal computer 12 and reads out the measurement data file 40 stored therein (S81).

At this time, in order to prevent illegal readout, when the person with authority to diagnose the patient enters a read request including a doctor code and a password by operating the keyboard 14 in response to a request for entry of a doctor code and a password (S82, S83), the entered doctor code and password are compared with the doctor code D14 and password D15 recorded in the memory card 15, and if they coincide with each other, the read request is verified, so that the blood pressure measurement data file 40 is read out from the memory card 15 (S84), and the measurement data group D3 and the analysis and judgment result data group D4 of the measurement data file 40 thus read out is displayed on the personal computer 12 (S85).

In the above description, it is assumed that the analysis and judgment data group D4 is previously generated in the blood pressure monitor 1, however, the analysis and judgment data group D4 may be generated in the personal computer 12. Specifically, the personal computer 12 may perform analysis and judgment in the same manner as described above on the basis of the measurement group data D3 of the blood pressure measurement data file 40, and the result may be displayed on the screen of the personal computer 12.

Since the person with authority to diagnose the patient diagnoses and determines a prescription for the patient while referring to the result of the analysis thus displayed, the contents are inputted from the keyboard 14 and the read out blood pressure measurement data file 40 and the inputted prescription contents are additionally registered in the patient record data file 10 which is previously fetched to the server apparatus 11 of the medical facility 7 or the personal computer 12 of the person with authority to diagnose the patient (S86). After completion of registration, the memory card 15 mounted on the memory card reader/writer 13 is initialized (S87).

It is to be understood that the above embodiments are for illustrative purposes only, and not intended to be limiting. The scope of this invention, therefore, is set forth in the claims and is intended to include any modifications within the equivalent meaning and scope of the claims.

What is claimed is:

1. An electronic blood pressure monitor, comprising:
    a measuring portion configured to measure a blood pressure of a subject;
    a first input interface for inputting time habit data of the subject to the blood pressure monitor, the time habit data being indicative of a daily habit pattern of the subject;
    a second input interface for inputting measurement pattern data to the blood pressure monitor, the measurement pattern data identifying a timing of a plurality of blood pressure measurements on the subject;
    a timing adjustment device for altering the timing of the measurements defined by the measurement pattern data based on the time habit data of the subject; and
    an output portion for outputting measurement data to an external device or an internal detachable data storage medium, the measurement data including results of the blood pressure measurements.

2. The blood pressure monitor of claim 1, further comprising an alarm device notifying a time of blood pressure measurement based on the timing altered by the timing adjustment device.

3. The blood pressure monitor of claim 1, wherein the timing of the blood pressure measurements defined by the measurement pattern data is configured to diagnose a type of hypertension of the subject.

4. The blood pressure monitor of claim 1, further comprising a first input portion providing the first input interface and a second input portion providing the second input interface, the second input portion being accessible only to a person with the authority to diagnose the subject.

5. The blood pressure monitor of claim 4, further comprising an event input interface for inputting event occurrence data into the blood pressure monitor, wherein the event input interface comprises a first event input portion disposed on the first input portion.

6. The blood pressure monitor of claim 4, further comprising an event input interface for inputting event occurrence data into the blood pressure monitor, wherein the event input interface comprises a second event input portion disposed on the second input portion.

7. The blood pressure monitor of claim 6, wherein the event occurrence data inputted by the second event input portion is used by the blood pressure monitor to display therapeutic instructions for the person with authority to diagnose the subject.

8. The blood pressure monitor of claim 6, wherein the event occurrence data inputted by the second event input portion is a record of administering medicine to the subject.

9. The blood pressure monitor of claim 8, further comprising,
    a memory portion storing data including the time habit data, the measurement pattern data and the measurement data, the measurement data being stored in the memory portion chronologically, and
    a computation portion which selects a set of the measurement data stored in the memory portion based on selection criteria for hypertension diagnosis, performs a computation on the selected data based on computation criteria for hypertension diagnosis, performs a judgment on a result of the computation based on judging criteria for hypertension diagnosis, and transfers a result of the judgement to the output portion,
    wherein the computation includes calculating a difference of the results of the measurements before and after a passage of a predetermined time from a start of the administering the medicine.

10. The blood pressure monitor of claim 1, further comprising a memory portion for storing data including the time habit data, the measurement pattern data and the measurement data, the measurement data being stored in the memory portion chronologically.

11. The blood pressure monitor of claim 10, further comprising an event input interface for inputting event occurrence data into the blood pressure monitor, the event occurrence data being stored in the memory portion chronologically.

12. The blood pressure monitor of claim 11, wherein an event corresponding to the event occurrence data has an influence on blood pressure measurements.

13. The blood pressure monitor of claim 10, further comprising a computation portion which selects a set of the measurement data stored in the memory portion based on selection criteria for hypertension diagnosis, performs a computation on the selected data based on computation criteria for hypertension diagnosis, performs a judgment on a result of the computation based on judging criteria for hypertension diagnosis, and transfers a result of the judgement to the output portion.

14. The blood pressure monitor of claim 13, further comprising an event input interface inputting event occurrence data into the blood pressure monitor, the event occurrence data being stored in the memory portion chronologically, wherein the computation includes calculating a difference of the results of the measurements before and after an occurrence of an event specified by the event occurrence data.

15. The blood pressure monitor of claim 13, wherein the result of the judgment is stored in the memory portion.

16. The blood pressure monitor of claim 13, wherein
    the plurality of the blood pressure measurements includes a first measurement performed when the subject wakes up, a second measurement performed when the subject completes a work day, and a third measurement performed when the subject goes to bed, and
    the computation includes dividing a result of the second measurement by a result of the third measurement or an average of a result of the first measurement and the result of the third measurement.

17. The blood pressure monitor of claim 13, wherein the plurality of the blood pressure measurements includes night-time measurements performed when the subject is asleep and day-time measurements performed when the subject is awake, and the computation includes calculating an average of results of the night-time measurements, calculating an average of results of the day-time measurements, a first day-time measurement and a last day-time measurement being excluded from the average calculation, and dividing the average of the results of the day-time measurements by the average of the results of the night-time measurements.

18. The blood pressure monitor of claim 13, wherein the plurality of the blood pressure measurements includes day-time measurements performed when the subject is awake, and the computation includes calculating an average of results of the day-time measurements, a first day-time measurement and a last day-time measurement being excluded from the average calculation, calculating an average of results of the first and last day-time measurements, and dividing the average of the results of the day-time measurements by the result of the last day-time measurement or the average of the results of the first and last day-time measurements.

19. The blood pressure monitor of claim 13, wherein the plurality of the blood pressure measurements includes night-time measurements performed when the subject is asleep and a day-time measurement performed when the subject completes a work day, and the computation includes calculating an average of results of the night-time measurements, and dividing the day-time measurement by the average of the results of the night-time measurements.

20. The blood pressure monitor of claim 13, wherein the plurality of the blood pressure measurements includes a first measurement performed when the subject wakes up and a second measurement performed when a predetermined time passes after the first measurement, and the computation includes dividing a result of the second measurement by a result of the first measurement.

21. The blood pressure monitor of claim 13, wherein the plurality of the blood pressure measurements includes day-time measurements performed when the subject is awake, and the computation includes calculating an average of results of the day-time measurements, a first day-time measurement and a last day-time measurement being excluded from the average calculation, and dividing a result of a blood pressure measurement performed on the subject when the subject is at a medical facility with the authority to diagnose the subject by the average of the results of the day-time measurements, the result of the blood pressure measurement performed at the medical facility being stored in the memory portion.

22. The blood pressure monitor of claim 21, wherein the blood pressure measurement at the medical facility is performed when a person with authority to diagnose the subject is present with the subject.

23. The blood pressure monitor of claim 10, wherein a readout from the memory portion is allowed only for the person with authority to diagnose the subject.

24. A blood pressure data processing system comprising:

an electronic blood pressure monitor configured to measure a blood pressure of a subject and to output measurement data including a result of a blood pressure measurement, the electronic blood pressure monitor including a memory portion for storing the measurement data; and an information processing system receiving the measurement data from the electronic blood pressure monitor, wherein the electronic blood pressure monitor comprises a timing adjustment portion which receives time habit data indicative of a daily habit pattern of the subject and measurement pattern data identifying a timing of a plurality of blood pressure measurements on the subject, and alters the timing of the measurements defined by the measurement pattern data based on the time habit data of the subject, and the information processing system comprises an information reception device for receiving the measurement data read out from the memory portion of the electronic blood pressure monitor in response to a read request and an output device outputting the measurement data received by the information receiving device.

25. The blood pressure data processing system of claim 24, wherein the electronic blood pressure monitor further comprises a computing portion performing a predetermined computation on the measurement data stored in the memory portion based on criteria for hypertension diagnosis and storing a result of the computation in the memory portion.

26. The blood pressure data processing system of claim 24, wherein the electronic blood pressure monitor further comprises an information sending portion sending the measurement data in response to the read request, the information processing system comprises a request sending portion sending the read request, and the information reception device comprises an information receiving portion for receiving the measurement data sent from the information sending portion.

27. The blood pressure data processing system of claim 24, wherein the electronic blood pressure monitor is configured to be directly connected to the information processing system by a data transmitting cable.

28. The blood pressure data processing system of claim 24, wherein the memory portion comprises a detachable storage medium, the electronic blood pressure monitor comprises a first medium access portion selectively engaging with the detachable storage medium and accessing the detachable storage medium engaged with the first medium access portion, and information reception device comprises a second medium access portion selectively engaging with the detachable storage medium and accessing the detachable storage medium engaged with the second medium access portion when the read request is inputted.

29. The blood pressure data processing system of claim 24, wherein the measurement data is read out only when the read request is verified.

30. The blood pressure data processing system of claim 24, further comprising a patient record registry device registering a patient record and a patient record management device managing the patient record, wherein the electronic blood pressure monitor further comprises an information sending portion for sending the measurement data read out from the memory portion, the patient record management device receives the measurement data sent from the information sending portion and stores the measurement data in the patient record registry device as a part of the patient record, and the information processing system receives a patient record of the subject stored in the patient record registry through the patient record management device and performs a predetermined computation on the measurement data based on criteria on hypertension diagnosis and the patient record of the subject.

31. The blood pressure data processing system of claim 30, wherein the blood pressure monitor is allowed to send the measurement data to the patient record management device only when the patient record management device verifies the blood pressure monitor.

32. The blood pressure data processing system of claim 30, wherein the blood pressure monitor is connected to the patient record management device via a communication network and a network connection device.

33. The blood pressure data processing system of claim 32, wherein the network connection device comprises a mobile communication terminal.

* * * * *